US010076460B2

(12) United States Patent
Harry et al.

(10) Patent No.: US 10,076,460 B2
(45) Date of Patent: *Sep. 18, 2018

(54) METHOD AND APPARATUS FOR IMPROVING HUMAN BALANCE AND GAIT AND PREVENTING FOOT INJURY

(71) Applicant: TRUSTEES OF BOSTON UNIVERSITY, Boston, MA (US)

(72) Inventors: Jason D. Harry, Rumford, RI (US); James J. Collins, Newton, MA (US); James B. Niemi, West Kingston, RI (US); Attila A. Priplata, Allston, MA (US); Stephen J. Kleshinski, Scituate, MA (US)

(73) Assignee: Trustees of Boston University, Boston, MA (US)

( * ) Notice: Subject to any disclaimer, the term of this patent is extended or adjusted under 35 U.S.C. 154(b) by 769 days.

This patent is subject to a terminal disclaimer.

(21) Appl. No.: 13/674,769

(22) Filed: Nov. 12, 2012

(65) Prior Publication Data

US 2013/0072835 A1    Mar. 21, 2013

Related U.S. Application Data

(63) Continuation of application No. 10/793,729, filed on Mar. 8, 2004, now Pat. No. 8,308,665.

(Continued)

(51) Int. Cl.
*A61H 1/00*    (2006.01)
*A43B 3/00*    (2006.01)
(Continued)

(52) U.S. Cl.
CPC .............. *A61H 1/00* (2013.01); *A43B 3/0005* (2013.01); *A43B 7/00* (2013.01); *A43B 7/1465* (2013.01);
(Continued)

(58) Field of Classification Search
CPC .. A61H 1/00; A61H 39/002; A61H 2205/125; A43B 7/00; A43B 7/1465;
(Continued)

(56) References Cited

U.S. PATENT DOCUMENTS 2,931,893 A    4/1960    Gonzalez et al.
3,731,674 A    5/1973    Parvin
(Continued)

FOREIGN PATENT DOCUMENTS

EP    0383685    *  8/1990    ............. A43B 13/18
JP    11-235372       8/1999
WO    2004/080528    9/2004

*Primary Examiner* — Quang D Thanh
(74) *Attorney, Agent, or Firm* — Nixon Peabody LLP

(57) ABSTRACT

A method and wearable system and for enhancing human balance and gait and preventing foot injury through neurological stimulation of the foot and the ankle. Subthreshold stimulation for neurosensory enhancement is provided via electrodes or vibrational actuators, or combination thereof, disposed in or on a wearable a platform, such as an insole, sock shoe, removable shoe insert, or applied without the support of a platform, to the skin surface of an individual. Suprathreshold stimulation for therapeutic purposes, such as improving blood flow, is also provided by the vibrational actuators. The actuators and electrodes are driven by bias signals generated by a bias signal generator that is coupled to a controller. The signal generator under the control of the controller is adapted to generate a non-deterministic random signal, a repetitive pattern or series of patterns. The controller optionally includes a communication port for interfacing with an external computer for purposes of optimizing and programming the controller. The wearable system is powered by a power source.

21 Claims, 28 Drawing Sheets

Related U.S. Application Data

(60) Provisional application No. 60/452,044, filed on Mar. 6, 2003.

(51) Int. Cl.

| | | |
|---|---|---|
| *A43B 7/00* | (2006.01) | |
| *A43B 7/14* | (2006.01) | |
| *A43B 13/00* | (2006.01) | |
| *A43B 17/00* | (2006.01) | |
| *A43B 19/00* | (2006.01) | |
| *A61F 5/01* | (2006.01) | |
| *A61F 5/14* | (2006.01) | |
| *A61H 39/00* | (2006.01) | |
| *A61N 1/04* | (2006.01) | |
| *A61N 1/20* | (2006.01) | |
| *A61N 1/32* | (2006.01) | |
| *A61N 2/06* | (2006.01) | |

(52) U.S. Cl.
CPC .............. *A43B 13/00* (2013.01); *A43B 17/00* (2013.01); *A43B 19/00* (2013.01); *A61F 5/0111* (2013.01); *A61F 5/14* (2013.01); *A61H 39/002* (2013.01); *A61N 1/0456* (2013.01); *A61N 1/0484* (2013.01); *A61N 1/0492* (2013.01); *A61N 1/20* (2013.01); *A61N 1/32* (2013.01); *A61N 2/06* (2013.01); *A61H 2205/125* (2013.01); *A61N 1/0468* (2013.01); *A61N 1/0476* (2013.01)

(58) Field of Classification Search
CPC ......... A43B 13/00; A43B 17/00; A43B 19/00; A43B 3/005; A61F 5/14; A61F 5/0111; A61N 1/0492; A61N 1/32; A61N 1/0456; A61N 1/0484; A61N 1/20; A61N 1/0468; A61N 1/0476; A61N 2/06
USPC ........ 601/22, 27, 30, 46, 48, 49, 57, 71, 79; 36/136, 140, 141
See application file for complete search history.

(56) References Cited

U.S. PATENT DOCUMENTS

| | | | |
|---|---|---|---|
| 3,765,422 | A | 10/1973 | Smith |
| 4,080,971 | A | 3/1978 | Leeper |
| 4,465,158 | A | 8/1984 | Yamazaki et al. |
| 4,569,352 | A | 2/1986 | Petrofsky et al. |
| 4,694,839 | A | 9/1987 | Timme |
| 4,979,502 | A | 12/1990 | Hunt |
| 5,181,504 | A | 1/1993 | Ono et al. |
| 5,203,793 | A | 4/1993 | Lyden |
| 5,374,283 | A | 12/1994 | Flick |
| 5,592,759 | A | 1/1997 | Cox |
| 5,766,236 | A | 6/1998 | Detty et al. |
| 5,913,838 | A | 6/1999 | Reilly |
| 5,974,344 | A | 10/1999 | Shoemaker, II |
| 6,027,463 | A * | 2/2000 | Moriyasu ................. 601/46 |
| 6,032,074 | A * | 2/2000 | Collins ................. A61F 7/00 607/2 |
| 6,059,576 | A | 5/2000 | Brann |
| 6,234,987 | B1 | 5/2001 | Chen |
| 6,290,661 | B1 | 9/2001 | Cutler et al. |
| 6,387,065 | B1 | 5/2002 | Tumey |
| 6,461,316 | B1 | 10/2002 | Lee et al. |
| 6,464,654 | B1 | 10/2002 | Montgomery et al. |
| 6,657,164 | B1 * | 12/2003 | Koch ................. A43B 7/04 219/211 |
| 6,876,947 | B1 * | 4/2005 | Darley ................. A43B 3/0005 324/160 |
| 7,152,345 | B2 | 12/2006 | Koenig |
| 2001/0045104 | A1 * | 11/2001 | Bailey, Sr. ........... A43B 1/0054 62/510 |
| 2004/0077975 | A1 | 4/2004 | Zimmerman |

\* cited by examiner

METHOD AND APPARATUS FOR IMPROVING HUMAN BALANCE AND GAIT AND PREVENTING FOOT INJURY

RELATED APPLICATION DATA

This application is a continuation application of pending U.S. patent application Ser. No. 10/793,729, filed Mar. 8, 2004, which is a non-provisional application of U.S. provisional patent application No. 60/452,044 filed Mar. 6, 2003, the contents of these applications being incorporated entirely herein by reference.

This invention was made with Government support under grants (AG08812, AG04390, DK60295, HD40035, and HD37880) awarded by the National Institutes of Health. The Government has certain rights in the invention.

BACKGROUND OF THE INVENTION

Field of the Invention

The invention relates to improving human balance and gait and preventing foot injury through neurological stimulation of the foot and ankle and more particularly to a wearable platform that provides neurological stimulation to the foot and ankle and to a system for optimizing neurological stimulation.

Description of Related Art

Various devices are available for foot support and injury prevention. For example, passive orthoses and braces are described in the art (e.g. U.S. Pat. No. 6,692,454 to Townsend et al. and U.S. Pat. No. 6,676,618 to Andersen). These rigid or semi-rigid devices are typically directed toward supporting the foot or ankle to prevent injury, correct skeletal alignment problems, or adjust posture. In so doing, they may effect beneficial changes in balance and gait, but do so by providing passive mechanical support.

Wearable massaging apparatuses for feet are also known. For example, wearable foot massagers are described in the art (e.g. U.S. Pat. No. 5,835,899 to Reilly, U.S. Pat. No. 5,913,838 to Reilly, and U.S. Pat. No. 6,464,654 to Montgomery). Massagers typically employ mechanical means of introducing significant deflections (i.e. suprathreshold stimulation) of the skin and subcutaneous tissue, including muscles.

Moreover, wearable foot heaters are described in the art (e.g. U.S. Pat. No. 6,657,164). These devices are typically directed toward pain relief, encouraging blood flow in skin, and maintaining thermal status of the foot, rather than to improving balance or gait. Heaters typically employ electrical resistance means to apply elevated temperatures directly to the skin of the foot.

Further, it has been found that the function of sensory cells in the human nervous system can be improved by inputting a noise signal to the sensory cell to effectively lower the threshold of the sensory cell. Since sensory cells are typically threshold-based units, lowering the sensory cell threshold decreases the level of outside stimulation needed to cause the sensory cell to respond (i.e. fire). Thus, the sensory cell will respond to outside stimulation at a lower level that would not result in a sensory cell response at normal cell threshold levels. U.S. Pat. Nos. 5,782,873 and 6,032,074 to Collins disclose a method and apparatus for improving the function of sensory cells by lowering the threshold of the sensory cells.

While these devices and methods fulfill their respective particular objectives and requirements, the aforementioned patents do not disclose a method and device for improving human balance and gait and preventing foot injury through neurological stimulation of the foot and/or ankle and more particularly a wearable system that provides neurological stimulation to the foot and/or ankle and to a system for optimizing the same.

BRIEF SUMMARY OF THE INVENTION

Balance, gait, and other coordinated movements of humans and other mammals rely on the real-time control of muscle contractions in response to volition and changes in the environment. This muscular control is coordinated by the central nervous system (CNS), i.e. the brain and spinal cord, but is reliant on sensory feedback from the extremities. Of primary importance are the mechanical senses that convey knowledge of skin contact with the environment and limb position.

Lack of adequate mechanical sensory feedback is strongly correlated to significant health problems in humans. These include, for example, the tendency of elderly individuals to fall and the occurrence of skin ulceration (open wounds) of the skin of the feet in people suffering from diabetes.

A collection of specialized sensory cells, called mechanoreceptors, is responsible for providing this flow of sensory information from the extremities. Mechanoreceptors transduce mechanical stimuli from the body's movements and interactions with the environment into electrical signals that can be transmitted and interpreted by the nervous system. Mechanoreceptors of various types, and found in various anatomic structures, have been identified by researchers in this field. For example, Pacinian corpuscles and other related sensory neurons, found in the skin and deeper subcutaneous layers, are sensitive to touch, stretch, pressure, and vibration ("tactile sense"). Other types of mechanoreceptors, e.g. Golgi tendon organs and muscle spindles, are found in tendons, ligaments, muscles, and tissues within joints. They convey information about muscle force, muscle stretch, and joint angles ("joint sense" or "proprioception").

Mechanoreceptors are threshold-based units. That is, if the environmental stimulus to the sensory cell is of insufficient magnitude, the cell will not activate and begin signaling. Such a stimulus is call "subthreshold." A stimulus that is above the threshold is called "suprathreshold."

Many health conditions and diseases (e.g. aging, diabetes, stroke, neuropathies, trauma and injury, etc.) can negatively impact either the sensitivity of the mechanoreceptors themselves, the transmission of nerve impulses (action potentials on axons), or the interpretation of nerve impulses centrally at the level of the spine or brain. Lost sensitivity of mechanoreceptors is essentially equivalent to a rise in the threshold level.

It is possible to improve the sensitivity of mechanoreceptors using particular forms of mechanical and electrical stimulation applied to the tissue in which the mechanoreceptors are found.

In view of the above, it is a general purpose of this invention and its various embodiments, which will be described in greater detail, to provide methods and apparatus to present forms of stimulation non-invasively to the surface of the skin as a means to improve or otherwise enhance mechanoreceptor performance. Further, it is a general purpose of this invention to serve as a therapy for individuals with degraded sensory performance. Still further, it is an additional purpose of the present invention to provide a massage therapy to improve blood flow to prevent or alleviate skin ulceration and the like.

Importantly, the invention and its various embodiments can be useful in those instances in which augmenting normal mechanoreceptor performance can compensate in part for problems of axonal transmission and CNS interpretation of sensory information. Similarly, enhancing the sensitivity of mechanoreceptors can be useful in improving overall sensorimotor performance in individuals with no neurological deficits.

The present invention advantageously provides novel methods and apparatuses for improving balance and gait by applying neurological stimulation to the soles and other surfaces of the feet. Further, the present invention advantageously provides novel methods and apparatuses for improving balance and gait by applying neurological stimulation to the ankle.

It is further an object of the present invention to provide novel methods and apparatus for reducing the likelihood of injuries to the foot, especially in individuals suffering from diabetic or other neuropathies, by applying neurological stimulation to the soles and other surfaces of the feet.

It is a further object of the present invention to provide novel methods and apparatus for improving general sensorimotor performance, including that required in normal or athletic activity, by applying neurological stimulation to the soles and other surfaces of the feet.

It is a further object of the present invention to provide novel methods and apparatus for improving balance, gait, and general sensorimotor performance and for reducing the likelihood of injuries to the foot by applying neurological stimulation to tendons, ligaments, and muscles about the ankle.

Additionally, an aspect of the present invention is that the neurological stimulation be of the sort, namely subthreshold, as described by Collins, in which the signal applied is either a non-deterministic random signal or a predetermined pattern that is repeated.

Another aspect of the present invention is that the neurological stimulation be suprathreshold, in which the signal applied is either a non-deterministic random signal or a predetermined pattern that is repeated.

Another aspect of the present invention is that the neurological stimulation be imparted either mechanically or electrically to the soles and other surfaces of the feet and/or to the ankle.

Another aspect of the present invention is to provide a wearable system for neurological stimulation of a foot and/or ankle, the system comprising a platform having at least one bias signal inputting means adapted to apply a stimulation to mechanoreceptors in the foot, at least one bias signal generator adapted to provide a driving signal to drive the at least one bias signal inputting means, a controller means for controlling the at least one bias signal generator and the at least one bias signal inputting means, and a power source providing electrical energy to the controller means and the at least one bias signal generator.

Another aspect of the present invention is to provide a wearable system that includes least one electrode placed on or near the foot and/or ankle that provides electrical stimulation to the mechanoreceptors of the foot and/or ankle.

Another aspect of the present invention is to provide a wearable system in which the bias signal inputting means is a stick-slip electrode system comprising an electrode pad incorporated in a garment, a hydrophilic and lubricious coating, a conductive hydrogel skin mount, and an adhesive layer.

Another aspect of the present invention is to provide a wearable system in which the wearable platform is a shoe, a boot, a sock, an insole portion integrally attached to the bottom of a sock, a removable insert of a shoe, a flexible disposable pad having a form of a foot with an underside coated with adhesive for removably attaching to a sole of a shoe, an ankle wrap, a customized structure adapted to position the bias signal inputting means in apposition to specific anatomical structures of the foot and/or ankle, or combinations thereof.

Another aspect of the present invention is to provide a wearable system that includes at least one bias signal inputting means as a vibrational actuator providing stimulating vibration to the mechanoreceptors of the foot and/or ankle.

Another aspect of the present invention is to provide a wearable system in which the platform comprises a flexible matrix material enclosing a vibration transmitting material and at least one of the actuators, and the platform is optimized for transmitting vibration to surfaces of the foot and/or ankle.

Another aspect of the present invention is to provide a wearable system in which the platform comprises a plurality of vibrational actuators disposed on the platform at a predetermined spatial separation between the plurality of actuators such that random vibration in the overall device may be induced by manipulating phase, amplitude, and wave shape of the driving signal of each vibrational actuator.

Another aspect of the present invention is to provide a wearable system in which the platform comprises a plurality of vibrational actuators adapted to create a vibration when being electrically biased, and wherein the controller means is adapted to operate the plurality of vibrational actuators in reverse of others so as to induce random vibrational stimulation.

Another aspect of the present invention is to provide a wearable system in which the platform comprises a plurality of vibrational actuators adapted to create a vibration when being electrically biased, and wherein the at least one bias signal generator is adapted to generate stepped driving signals, wherein the duration of each step of the driving signals is of a time duration sufficient to avoid placing the actuators in its natural frequency of vibration.

Another aspect of the present invention is to provide a wearable system in which the platform comprises a plurality of actuators adapted to create a vibration when being electrically biased, and wherein the at least one bias signal generator is adapted to generate an offset driving signal in addition to the driving signal so as to place the actuators in an inertia-overcoming state to improve the time responses of the actuators.

Another aspect of the present invention is to provide a wearable system in which the bias signal generator is adapted to generate an offset driving signal in addition to the driving signal so as to place the actuators in an inertia-overcoming state to improve the time responses of the actuators when the actuators are being driven in reverse polarity of the others.

Another aspect of the present invention is to provide a wearable system in which a plurality of vibrational actuators disposed on the platform at a predetermined spatial separation between the plurality of actuators to induce a vibration having a desirable amplitude by manipulating phase and amplitude of the driving signal of each vibrational actuator.

Another aspect of the present invention is to provide a wearable system in which the vibration transmitting material comprises at least one of rigid beads, polymeric gel, a viscoelastic foam, a metallic structural element, and a composite structural element and is arranged in such a way as to effect adjustable vibration propagation, and a plurality of actuators positioned at a predetermined spatial separation between the plurality of actuators to optimize the vibration propagation characteristics of the platform.

Another aspect of the present invention is to provide a wearable system in which the signal generator provides a signal of a predetermined at least one repetitive pattern and series of patterns with controllable signal amplitude, frequency content, waveform shape, and repetition.

Another aspect of the present invention is to provide a wearable system in which stimulations are alternately provided at a sub-threshold level and a supra-threshold level, so as to effect sensory enhancement, therapeutic massage and improvement of blood flow.

Another aspect of the present invention is to provide a wearable system comprising means for determining gait cycles so as to place the system under a power conservation mode during predetermined phases of a predetermined gait cycle.

Another aspect of the present invention is to provide a wearable system comprising a thermal radiation source for providing heating to the foot, in addition to the means for stimulating the mechanoreceptors of the foot/ankle.

Another aspect of the present invention is to provide a wearable system comprising adjusting means for a wearer to adjust the amplitude of the bias signal, including threshold and therapeutic levels.

Another aspect of the present invention is to provide a system for optimizing neurological stimulation which includes a wearable platform having at least one bias signal inputting means adapted to apply a stimulation to a skin surface area of a test subject, at least one bias signal generator adapted to provide a driving signal to drive the at least one bias signal inputting means, a controller means for controlling the at least one bias signal generator and the at least one bias signal inputting means, a remote external computer for effecting the control of the controller means during an optimization procedure, a communication means between the remote external computer and the controller, and a measurement means for measuring the responses of the test subject as stimulation is adjusted, wherein the remote external computer is adapted to communicate with the controller to effect varying bias signals inputted into the at least one bias signal inputting means, while responses from a subject in contact with the platform and executing a prescribed task are observed and measured, wherein the remote computer is adapted to determine the optimal bias signal parameters suitable for the subject based on the observed responses of the subject, wherein the remote external computer selects bias signal parameters to test based on responses of the subject, and the remote external computer includes means for receiving and recording responses from the subject for each bias signal applied.

Another aspect of the present invention is to provide method for providing neurological stimulation in a wearable system which includes the steps of providing a wearable platform having one or more sources of stimulation, at least one signal generator coupled to the one or more sources of stimulation, a controller for controlling the signal generator, and a power supply source for powering the controller, selecting a level or form of stimulation, and activating the signal generator and supplying a bias signal to the one or more sources of stimulation to stimulate mechanoreceptors based on a determined therapeutic need of an individual, wherein the step of selecting a level or form of stimulation comprises measuring an individual's threshold level of sensation in the area to receive stimulation and adjusting or programming the controller to control the bias signal generator to produce a therapeutic level relative to the measured threshold level and according to a therapeutic need of an individual, and wherein the measuring of a threshold level comprises a tracking procedure which begins with a minimal or maximal signal and makes incremental changes towards the final threshold based on an individual's response.

Other aspects of the present invention will be apparent in the description of each embodiment discussed hereafter.

BRIEF DESCRIPTION OF THE DRAWINGS

The invention will be better understood and aspects of the inventions other than those set forth above will become apparent when consideration is given to the following detailed description thereof.

FIG. 3b is an expanded view of the ankle cuff shown in FIG. 3a.

FIG. 4b is a side view of the harness shown in FIG. 4a.

FIG. 5b is a bottom plan view of an insole-like portion of the garment-like device in FIG. 5a.

FIG. 9b is a side view of an embodiment of the structure in FIG. 9a.

FIG. 9c is a side view of another embodiment of the structure in FIG. 9a.

FIG. 9d is a side view of another embodiment of the structure in FIG. 9a.

FIG. 9e is a side view of an embodiment of the structure in FIG. 9a.

DETAILED DESCRIPTION OF THE INVENTION

Figure 1A:
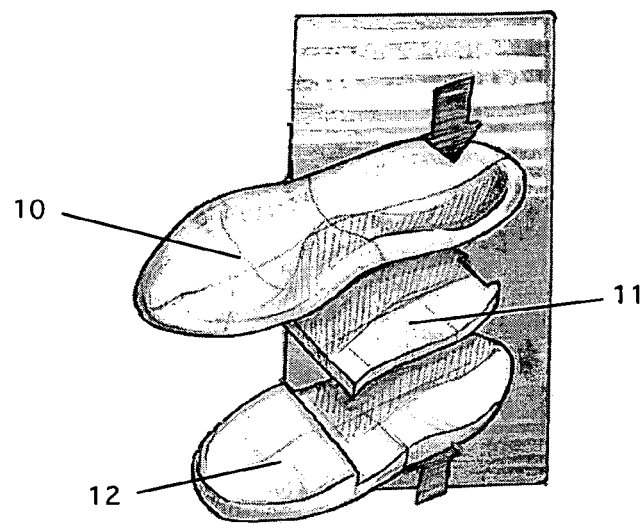
FIG. 1a is an exploded view of a shoe insole insert according to a first embodiment of a wearable neurological stimulation device of the present invention.

Throughout this specification and the drawing figures associated with this specification, numerical labels of previously shown or discussed features may be reused in another drawing figure to indicate similar features.

Figure 1B:
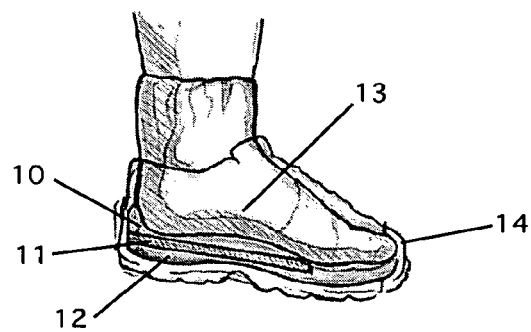
FIG. 1b is a side view of the insole insert of FIG. 1a inserted into a shoe.
Figure 1C:
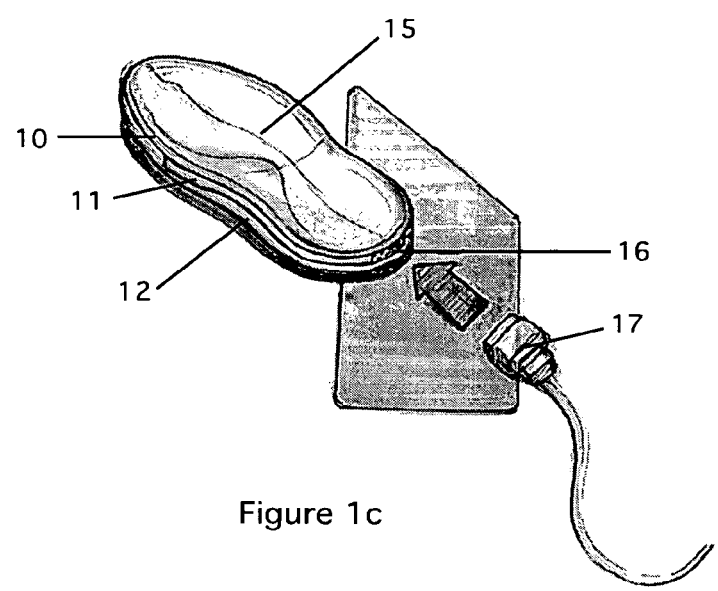
FIG. 1c is a perspective view of the insole insert according to the first embodiment of the present invention.

With reference now the drawings, FIGS. 1a-1c illustrate a first embodiment of a wearable system of the present invention in the form of a shoe insole insert. FIG. 1a depicts an exploded view of the insole insert device that is constructed of several layers. The top layer 10 of the insole is a conformable flexible layer which provides a comfortable interface between the foot and actuator components. This top layer 10 has typical foot contours and variations in thickness found on traditional insoles. It typically is made of foam, cloth, or gels. The intermediate layer 11 is an enclosure containing a rechargeable battery source and a control pod with signal generation circuitry, which are not shown for the purpose of clarity and simplification of the drawing. Details of the battery, control pod, and signal generation circuitry will become more apparent with the teachings of this and other embodiments of the present invention.

A bottom layer 12 shown in FIG. 1a is comprised of a material that can propagate vibration efficiently. Actuators for generating a vibrational stimulus may be incorporated in any of the layers but traditionally would not be included in the comfort top layer 10. The actuators, not shown, are comprised of one type or a combination of types of actuators, including electromagnetic, electro-mechanical, solid state actuators (e.g., Nitinol, piezoelectric), hydraulic, pneumatic, ferrofluid, electroactive polymer, etc. The actuators are driven by the signal generation circuitry to produce a nondeterministic, noisy, or deterministic signal (i.e. bias signal) at the surface of the foot through the insole material layers. The bias signal can be of a subthreshold or a suprathreshold level. Details of the driving signal generated by the signal generator and the bias signal from the actuators, as well as the ranges of bias signal frequency, will be further disclosed in another teaching section relating to the controller in this specification.

The vibrational multilayer structure of FIG. 1a is controllable via a controller for the therapeutic stimulation level for each foot 13 during a fitting session and inserted into their shoe 14 for use.

FIG. 1b depicts the vibrational insole insert being used in a shoe 14 to provide stimulation to foot sole. Following use, the battery power source in the insole can be recharged using the interface port 16 and an external charging cable 17 shown in FIG. 1c. The interface may also include a communication interface for coupling a controller with an external device for remote external control, diagnostic, tuning, programming, and other purposes.

FIG. 1c depicts the completed assembly and programming interface of the multilayer insole insert of FIG. 1a. As previously mentioned, the interface port 16 may also serve as a programming port, allowing vibration levels and signals to be altered, for example. The communication interface may be a wired or optical serial or parallel communication. The communication interface may also be a wireless RF or optical communication means.

The insole insert in FIGS. 1a-1c described above includes vibrational stimulators. However, the top layer 10 can also be adapted to accommodate electrical stimulators, which may be used in conjunction with a combination of one or more vibrational actuators located in or on the other aforementioned layers.

For electrical stimulation, one or more of disposable, reusable, or stick-slip electrodes may be used. As previously mentioned, the stimulation provided is of a subthreshold level, a suprathreshold level, or alternating between the two levels as allowed by the types of stimulator used.

While wearing the active neurological stimulation insole in FIGS. 1a-1c in the shoe, the user will enjoy an improvement in tactile sensitivity at the bottom of the foot. This improved tactile sensitivity will lead to improved balance, improved gait, enhanced sensorimotor performance, reduction of falls, and prevent injury such as diabetic foot ulcers.

FIGS. 1a-1c depict an insole structure for delivering neurological stimulation to the sole of the foot. A more general embodiment of this aspect of the present invention is that the stimulation platform can be any insert that is placed into a shoe, more specifically to deliver stimulation to the sides and top surfaces of the foot, in addition to or instead of the sole of the foot.

Figure 2A:
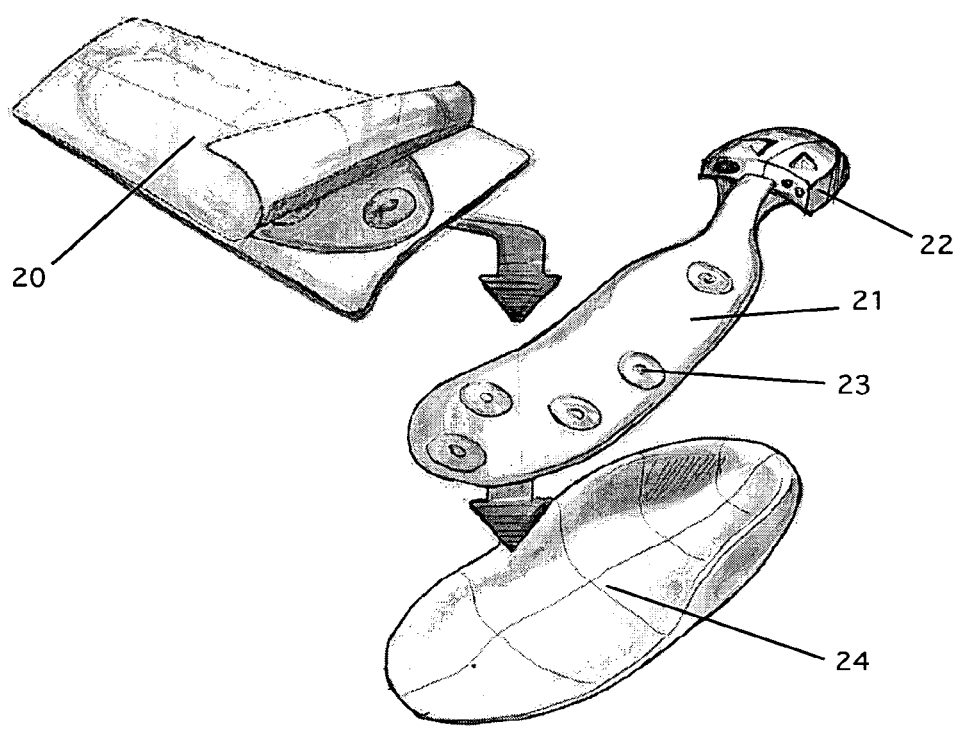
FIG. 2a is an overall perspective view of a disposable pad according to a second embodiment of a wearable neurological stimulation device of the present invention.
Figure 2B:
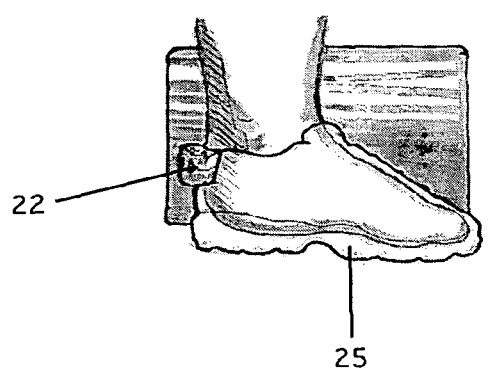
FIG. 2b is a side view of the disposable pad of FIG. 2a inserted into a shoe.

FIGS. 2a and 2b depict a second embodiment of the present invention. FIG. 2a illustrates an insole device including a disposable flexible pad 21 packaged in a disposable pouch 20. The device comprises of an insole pad 21 that is constructed of a thin conformable flexible layer containing thereon several electrode sites 23. A plurality of stimulation electrodes is incorporated in the electrode sites 23 on the top side of the pad facing the bottom of the foot. Stimulation electrodes may include, for example, disposable electrodes, re-useable electrodes to be used with conductive gel, or a new novel electrode design known as a stick-slip electrode system, which will be described in greater detail below.

These plurality of stimulation electrodes are coupled to a controller housed in a housing 22. Housing 22 also includes a power source, a signal generator, and a controller controlling the signal generator. The controller may also include user interface controls. This controller produces a nondeterministic signal, or alternatively a nondeterministic waveform, which results in random noisy subthreshold stimulation of the foot in contact with pad 21 and its stimulation electrodes. One or more reference electrodes may be included in the top layer of the pad 21, or on other parts of the body of an individual. The pad 21 is preferably thin and replaceable and can be added to an insole 24 to generate contours for comfort. A self-adhesive layer or a non-slip layer may be applied to the bottom side of the pad to prevent the pad from moving in relation with insole 24 during use.

FIG. 2b depicts the insole device of FIG. 2a being used in shoe 25. The housing 22 is mounted on the back of shoe for convenience. Alternatively, the housing with the controller and other essential components may be mounted on the sides or top of the shoe. The controller with the signal generator and the battery may also be removably coupled to the disposable insole insert via an extension connector, not shown, such that these components can be located at other another locations other than on the shoe. An advantage of having a removable coupling is that the controller, the signal generator, and the battery may be reused while the insole insert may be discarded and replaced as it is worn out from use.

The disposable flexible pad 21 in FIG. 2a described above includes electrical stimulators. However, the pad 21 can also accommodate vibration actuators or a combination of one or more electrodes and one or more vibrational actuators. Further, similar to the first embodiment in FIGS. 1a-1c of the present invention, a communication interface port and a power recharging port may also be advantageously included.

Figure 3A:
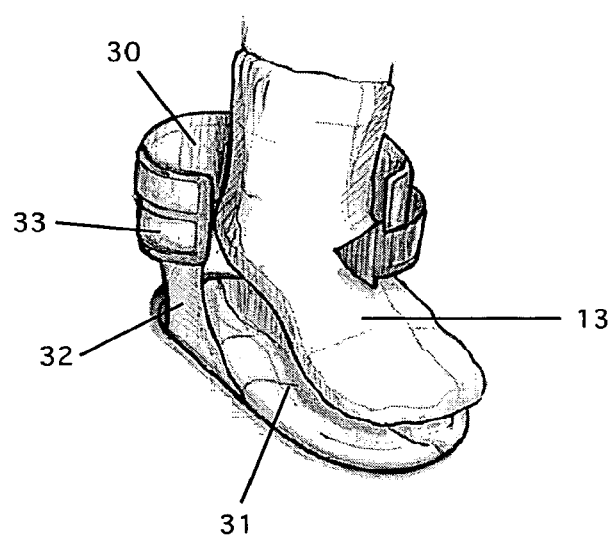
FIG. 3a is a perspective view of a third embodiment of a wearable neurological stimulation device of the present invention.
Figure 3B:
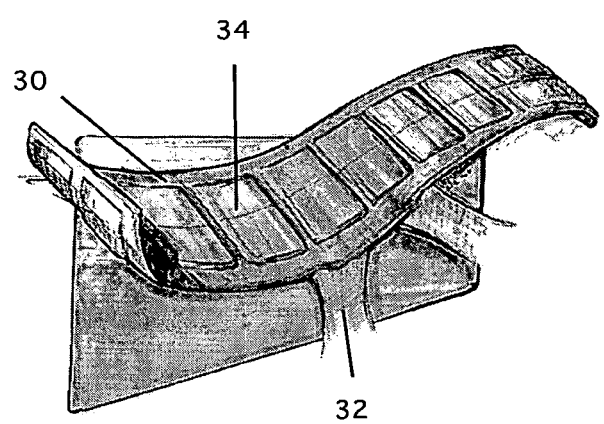

FIGS. 3a and 3b depict a third embodiment of the present invention. FIG. 3a illustrates a stimulating device that comprises an ankle cuff 30 connected via a connector assembly 32 to a stimulating layer 31. Stimulating layer 31 is a platform for carrying stimulation electrodes and/or active vibrational actuators for applying stimulation to the plantar surface of the foot 13. Ankle cuff 30 houses electronic components connected to the stimulation electrodes and/or active vibrational actuators providing electrical or mechanical stimulation, respectively. The ankle cuff is wrapped around the ankle and its position is maintained by a fastening device 33, such as a hook-and-eye, Velcro strips, or a clasp, for example, while in use.

FIG. 3b depicts an expanded view of the ankle cuff of FIG. 3a. The material of the cuff is preferably soft and conformable and contains pockets 34 for batteries and controlling electronics circuitry. The ankle cuff 30 may also include stimulation electrodes or vibrational actuators for applying stimulation to areas around the ankle. Further, similar to the first embodiment in FIGS. 1a-1c and the second embodiment in FIGS. 2a-2b of the present invention, a communication interface port and a power recharging port may also be advantageously included with the ankle cuff 30 in this stimulating device.

Similar to the first and second embodiments of the present invention, for electrical stimulation, one or more of disposable, reusable, or stick-slip electrodes may be used. For mechanical stimulation, one or more actuators of type electromechanical, electromagnetic, solid-state, hydraulic, pneumatic, ferro-fluid, electroactive polymers, and other actuator types may be used to deliver vibration. In either case, electrical or mechanical the stimulation signal is a nondeterministic signal, and may be of a subthreshold level, a suprathreshold level, or alternating between the two levels as allowed by the types of stimulator used.

Figure 4A:
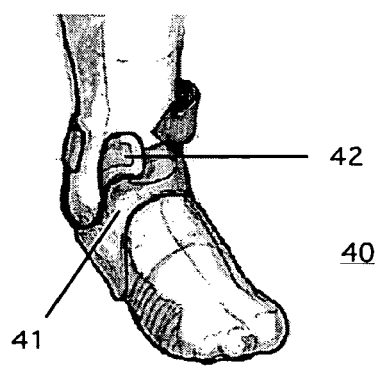
FIG. 4a is a perspective view of a foot and ankle harness according to a fourth embodiment of a wearable neurological stimulation device of the present invention.
Figure 4B:
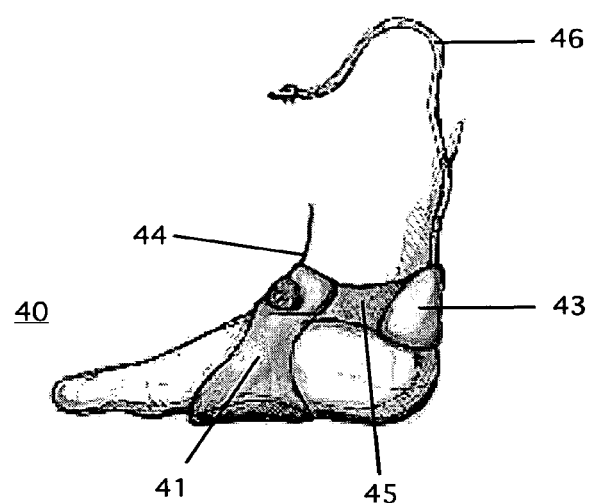

FIGS. 4a and 4b illustrates a fourth embodiment of the present invention. FIG. 4a is generally a frontal view of a harness 40 for providing neurological stimulation to the foot and ankle. The harness includes a frontal portion worn on a foot and a fastener means 42 for securing the harness 40 around the ankle. The harness 40 serves as a platform for applying stimulation to various areas of the foot and ankle through stimulating electrodes, vibrational actuators, or a combination thereof. The harness 40 may be worn with standard footwear.

As shown in FIG. 4b, which is a side view of the harness in FIG. 4a, the harness 40 includes a connecting portion 45 linking a back portion 43 with the frontal portion 41 and securing the harness firmly and comfortably to the foot and ankle. The connecting portion 45 may be, for example, a stretchable fabric, meshes, viscoelastic foams, or gels. Mounted on the back portion 43 and the frontal portion 41, and optionally on the connecting portion 45, are stimulation means, such as electrical signal stimulator and mechanical vibrational stimulator discussed above in relation to the first, second, and third embodiments. The locations of the stimulation means include the front of the ankle 44, the back, and may include the side to target tendons, ligaments, and muscles responsible for ankle movement and stability.

Similar to the embodiments set forth above, for electrical stimulation, one or more of disposable, reusable, or stick-slip electrodes may be used. For mechanical stimulation, one or more actuators of type electromechanical, electromagnetic, solid-state, hydraulic, pneumatic, ferro-fluid, electroactive polymers, and other actuator types may be used to deliver vibration. In either case, electrical or mechanical the stimulation signal is a nondeterministic signal, and may be of a subthreshold level, a suprathreshold level, or alternating between the two levels as allowed by the types of stimulator used.

Further, as shown in FIG. 4b, the harness is electrically detachably connected to a remotely located controller, including a signal generator, a battery and optionally a communication interface via a cable 46. The detachable harness can be discarded and replaced as a wear-and-tear item while the more durable electrical and electronic components can be reused. Alternatively, all of these components may be advantageously integrated with the harness 40 to form a compact wearable unit. In such an integrated configuration, the cable 46 may be used as a removable cable used for programming the controller or recharging the battery.

Figure 5A:
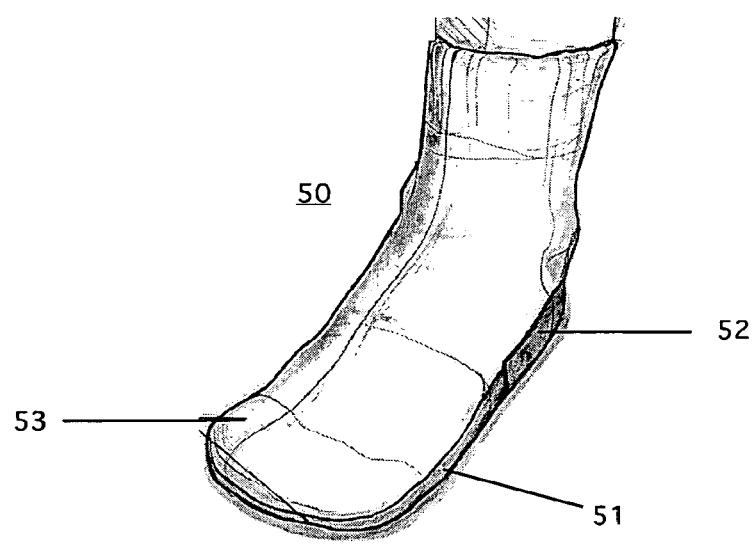
FIG. 5a is a perspective view of a garment-like device according to a fifth embodiment of a wearable neurological stimulation device of the present invention.

FIGS. 5a-5d illustrate a fifth embodiment of the present invention. FIG. 5a shows a garment-like device 50 with a sock-like top member 53 and an insole-like bottom member 51. The insole-like bottom member 51 consists of a moveable interface region 52 for moveably and detachably coupling with bias signal generator of a controller housed in a heel insert 55 shown in FIG. 5c.

Figure 5B:
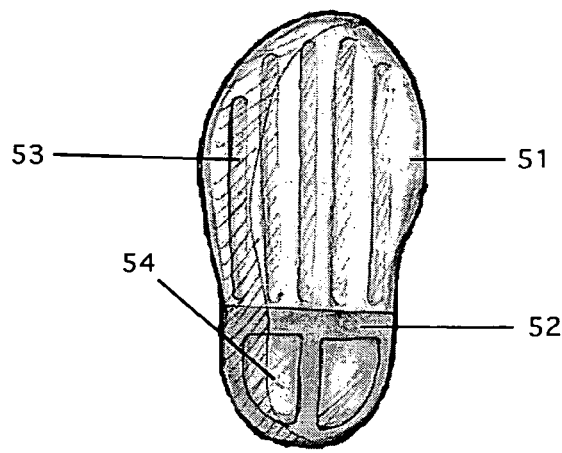

FIG. 5b shows a view from the bottom side of the insole-like bottom member. From this view, it is apparent that the interface region 52 comprises two connector pads 54. The connector pads 54 are connected to an electrode pattern 53 woven or insertable into the insole-like bottom member 51. The electrode pattern 53 makes contact with the skin of the foot of the individual wearing the device to provide electrical stimulation when a bias signal is applied to the connector pads 54.

Figure 5C:
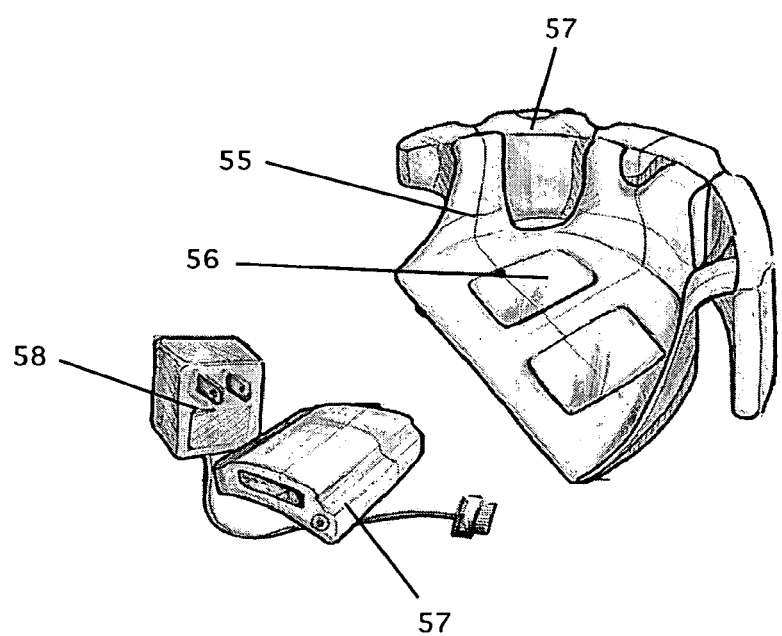
FIG. 5c is a perspective view of a heel insert according to a fifth embodiment of a wearable neurological stimulation device of the present invention.
Figure 5D:
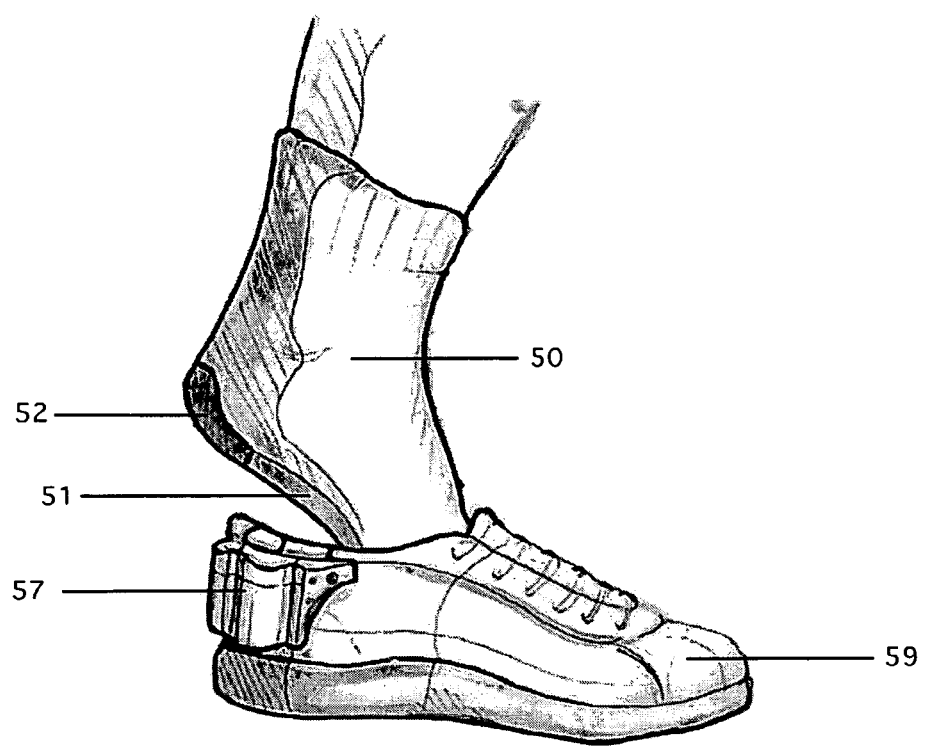
FIG. 5d is a side view of the garment-like device of FIGS. 5a and 5c.

The heel insert 55 shown in FIG. 5c includes a pair of contact pads 56 for receiving the two connector pads 54 of the insole-like bottom member 51. An integral part of the heel insert 55 is a housing 57 for a battery power source and the controller and its associated bias signal generator. In use, the heel insert 55 is fixedly or removably attached to a shoe 59 at the shoe's back and heel area, as shown in FIG. 5d. Then, the foot wearing the garment-like device 50 is inserted into the shoe 59. Once inserted, an electrical connection between the two connector pads 54 on the insole-like bottom member 51 and the pair of contact pads 56 on the heel insert 55 is made thus completing a circuit allowing stimulating electrical signals to flow to the electrodes woven into the insole-like bottom member 51.

The battery power source in the housing 57 is preferably a rechargeable power source that can be recharged using a recharger 58 shown in FIG. 5c. In addition, the controller in the housing 57 can be programmed using a cable or a wireless connection to external computer device, not shown.

The connection between the two connector pads 54 on the insole-like bottom member 51 and the pair of contact pads 56 on the heel insert 55 may be improved through the use of slight amounts of conductive gel. The pads 54 in the moveable interface region 52 have sufficient dimension to allow some movement of the sock structure within the shoe without disrupting the connection. Further, the controller in the heel insert 55 of the device can be used to adjust electrical stimulation levels to a therapeutic level.

The moveably and detachably electrical coupling between the insole-like bottom member and the heel insert is conveniently allow a wearer of the garment-like device to easily slip in and out of a footwear when desired. Further, the garment-like device may be easily washed without damaging any electronic component, and it may be discarded and replaced as a wear-and-tear item while the more durable heel insert is reused. Moreover, if the heel insert 57 is removeably attached to a shoe, the heel insert then has increased portability which allows it to be portable to a new shoe when desired.

Figure 6:
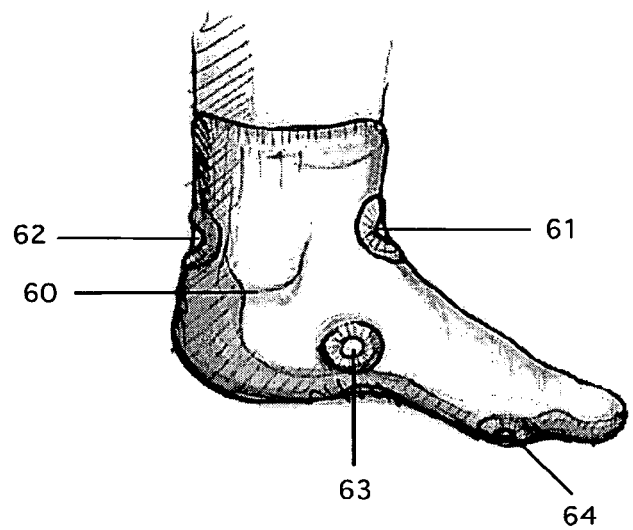
FIG. 6 is a side view of a sock-like device according to a sixth embodiment of a wearable neurological stimulation device of the present invention.

FIG. 6 depicts a sixth embodiment of the present invention. As shown therein, a sock 60 to be worn on the foot includes a number of pockets or regions to accommodate stimulators. Depending on the needs of the individual, stimulation devices can be located on the front of the ankle 61, to stimulate the tibialis anterior tendon, on the back of the ankle 62 to stimulate the Achilles tendon, on the side of the foot 63, or on the sole of the foot 64.

The stimulation locations are designed to include both mechanical actuators for vibrational stimulation and/or electrodes for electrical stimulation. In a configuration wherein electrical stimulation is provided to the foot and/or ankle, the sock provides electrode locations for proper user compliance and electrode placement. Conductive wires run throughout the sock, eliminating visible wires. Inserting the foot into a specially made shoe connects the sock to a controller and battery located in the sole of the shoe. The controls for this sock may be located on the side of the shoe.

An advantage of the sock 60 for is that the controller, the signal generator, and the battery integrated with the shoe may be reused while the sock may washed and may be discarded and replaced as it is worn out from use. Similar to the previously discussed embodiments of the present invention, the shoe may have a battery charging port for charging the battery and a communication interface port for connecting with a remote external computer device for purposes such as diagnostics, tuning, and programming.

The stimulators are driven by the signal generation circuitry to produce a nondeterministic or noisy signal (i.e. bias signal) at the surface of the foot and/or ankle. The bias signal can be of a subthreshold or a suprathreshold level. For electrical stimulation, one or more of disposable, reusable, or stick-slip electrodes may be used. As previously mentioned, the stimulation provided is of a subthreshold level, a suprathreshold level, or alternating between the two levels as allowed by the types of stimulator used. Further, similar to the effects achieved by using the aforementioned embodiments of the present invention, by stimulating the bottom of the foot one can expect to improve tactile sensation. By stimulating the ankle region one can expect to improve proprioception, or joint angle sense, which will have a direct effect on balance and gait. By combining stimulation, one can enjoy balance, gait, and tactile sense improvements on the foot. In addition, the device could be used to deliver a supra threshold level therapeutic massage for the purposes of improving blood flow.

Figure 7:
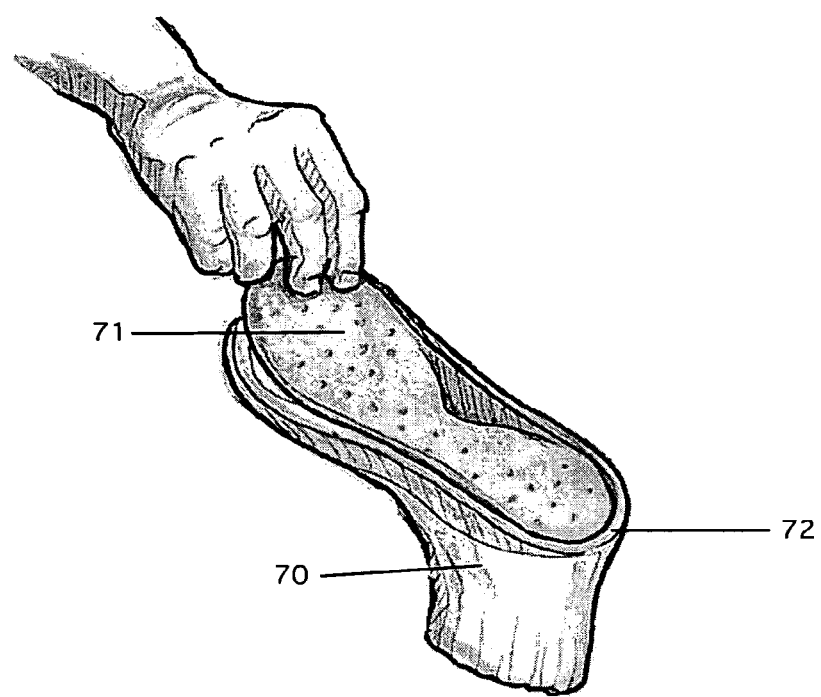
FIG. 7 is a bottom perspective view of a seventh embodiment of a wearable neurological stimulation device of the present invention.

FIG. 7 is an illustration of a seventh embodiment of the present invention providing a stimulating structure for stimulating the bottom of a foot sole. In this embodiment, a stimulating insole is a disposable electrode pad 71 that adheres to the surface of a sock 70. The sock provides an electrical connection to a controller and a battery power source through conductive materials. In use, the individual would evert the sock 70, remove the disposable electrode pad 71 from a package, mount it on the inside bottom of the sock 70, and re-evert the sock. The insole would be a very flexible or comfortable structure allowing to the insole to be used during the day when placed in a shoe or will also provide benefit without the shoe as long as the sock is worn. The stimulating insole may be entirely self contained or may be connected to an exterior controller via a cable for power and signal generation. The insole can be disposed of when the sock is washed or reused for some definite period of time.

Although not shown in FIG. 7, a similar structure could be configured and applied to provide stimulation to the side and top surfaces of the foot.

Figure 8A:
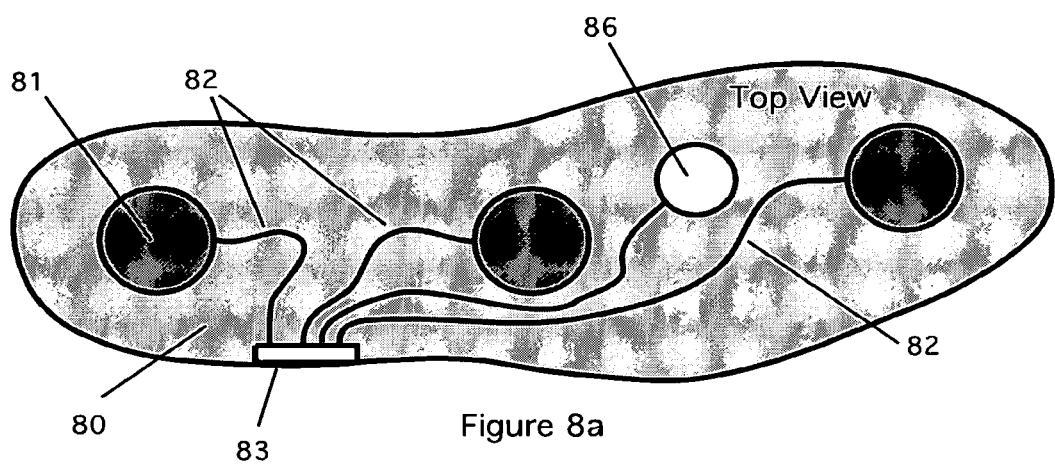
FIG. 8a is a top view depicting a shoe insert with the incorporation of vibrational actuators and thermal elements.

FIGS. 8a-e depict additional embodiments of the present invention. Shoe inserts that apply mechanical neurological stimulation, whether of an insole type as shown in FIG. 8a or of a type that more substantially surrounds the foot, utilize vibrational actuators to create the bias signal. These actuators can be incorporated into the insert in several ways. FIG. 8a shows one or more individual actuators 81 placed at locations throughout the insert 80. Actuator locations can preferably be based on foot anatomy (considering, for example, the roles that mechanoreceptors in different locations play in balance and gait), and design considerations (for example, needing to maintain flexibility in certain places).

As the actuators are powered by electricity, they must be connected to a power source with conductors 82, as shown in FIG. 8a. These conductors may be formed from wires or may be patterned, for example, on a flexible electric circuit that is provided as a layer in the insert. The conductors will preferably be terminated at a connector 83 that is incorporated into the insert. A mating connector wired from the controller would be used to establish electrical connection to the insert.

Figure 8B:
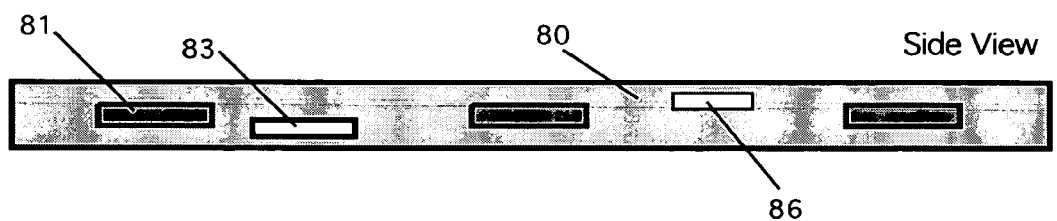
FIG. 8b is a side view of an embodiment of the shoe insert of FIG. 8a with the incorporation of vibrational actuators and thermal elements.

As shown in FIG. 8b, the actuators 81 are preferably embedded within the material of the shoe insert. As some types of actuators are rigid, it may be preferable to remove them from the skin-contact side of the insert.

Figure 8C:
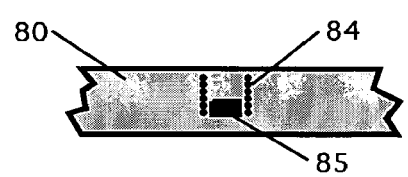
FIG. 8c is a side view of an embodiment of components of a linear electromagnetic actuator incorporated directly into the shoe insert material.

The actuators 81 may be constructed as independently operating units that are embedded into material of the insert 80. It may be preferable to embed components of the actuator directly into the insert material, effectively using the insert material as the housing of the actuator. In FIG. 8c, internal components of a linear electromagnetic actuator are depicted. A coil of wire 84 and a permanent magnet 85 are embedded directly into the material of the insert. Similarly, other actuator types may be effectively realized by embedding their constituent components directly in the insert material.

Figure 8D:
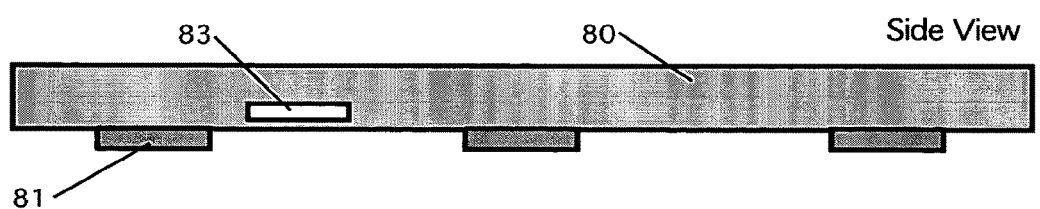
FIG. 8d is a side view of an embodiment of the shoe insert of FIG. 8a with vibrational actuators mounted on an outer surface of the shoe insert.
Figure 8E:
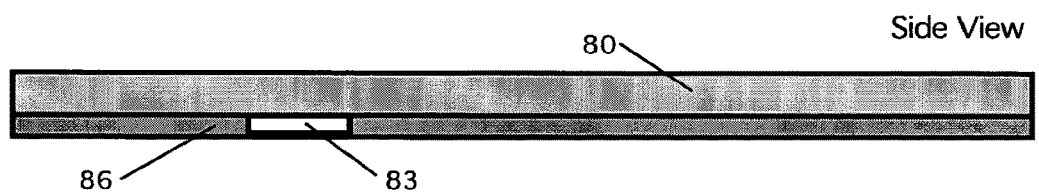
FIG. 8e is a side view of another embodiment of the shoe insert of FIG. 8a with vibration actuators mounted on an outer surface of the shoe insert.

Another preferred embodiment of the present invention is to locate the actuators 81 on the surface of the shoe insert material, as shown in FIG. 8d. Yet another preferred embodiment is to bond the insert material 80 to a thin, planar solid-state actuator 86 (for example, piezo-electric film, electro-active polymer, etc.). In certain instances, notably electro-active polymers, the actuator may form substantially the entire insert.

Figure 9A:
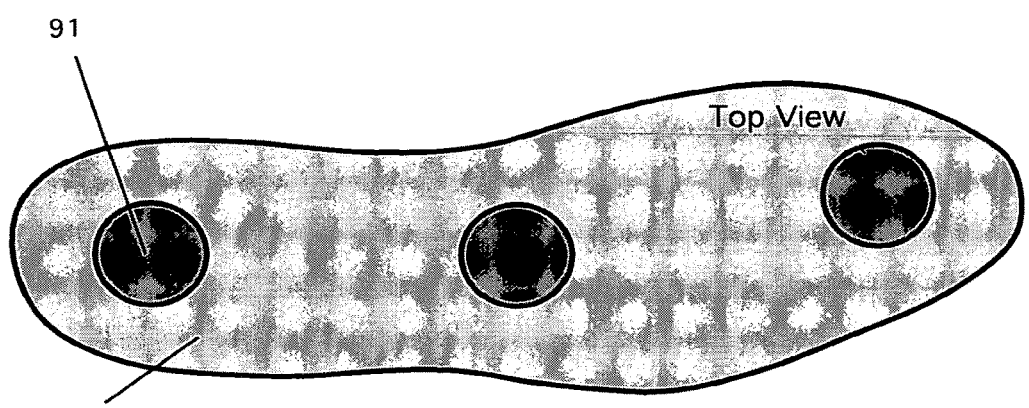
FIG. 9a is a top view of a structure that combines vibrational actuators and vibration propagation means in a shoe insert.
Figure 9B:
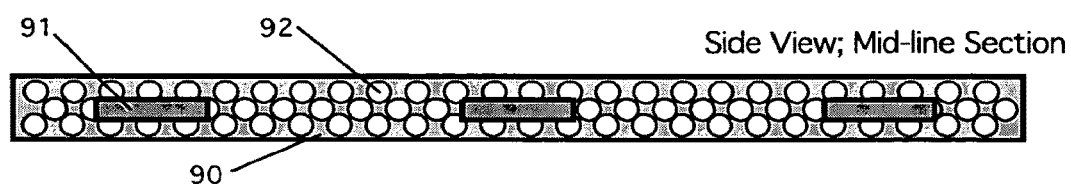
Figure 9C:
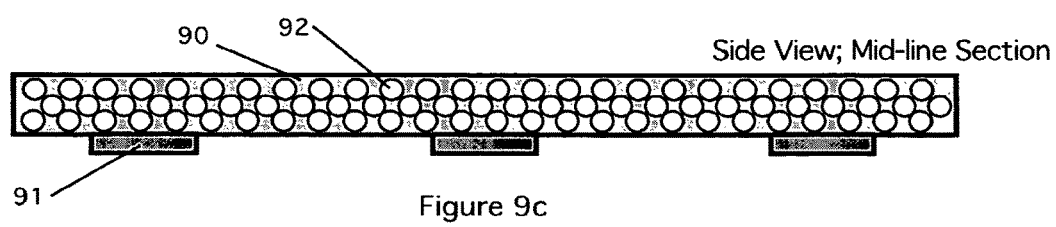
Figure 9D:
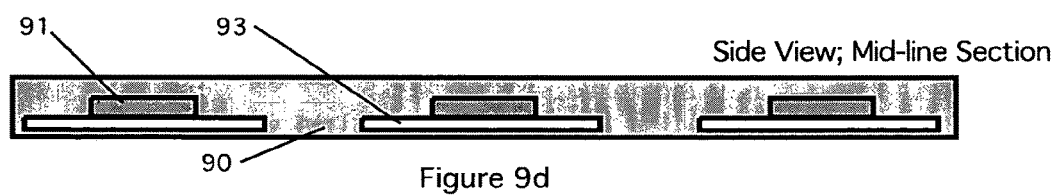

FIGS. 9a-e depict additional embodiments of the present invention. Shoe inserts that apply mechanical neurological stimulation, whether of an insole type as shown in FIG. 9a or of a type that more substantially surrounds the foot, utilize vibrational actuators to create the bias signal. Vibrations emanating from the actuators 91, whether located within the insert material, as shown in FIGS. 9b and 9d, or affixed to a surface of the insert material (FIGS. 9c and 9e), are meant to propagate throughout the material of the insert 90 to provide neurological stimulation over the largest possible skin area. Yet, in order to be comfortable, the material of the insert should preferably be flexible and compressible, material characteristics that are often not well suited to vibration propagation. It is possible to improve vibration propagation throughout the insert by embedding structures of materials with mechanical properties (e.g. stiffness and damping ratio) selected such that they can serve as pathways for vibration to travel away from the actuators with less attenuation.

One such embedded structure is a multiplicity of small, rigid beads 92 distributed throughout the surrounding matrix material of the insert (FIGS. 9b and 9c). The beads serve to transmit vibration while allowing the insert to remain substantially flexible and compressible. The beads may be densely packed, in layers or throughout the matrix material, or may be less densely packed. The beads may also be non-rigid, but nonetheless with properties more conducive to vibration propagation than the surrounding matrix material.

Figure 9E:
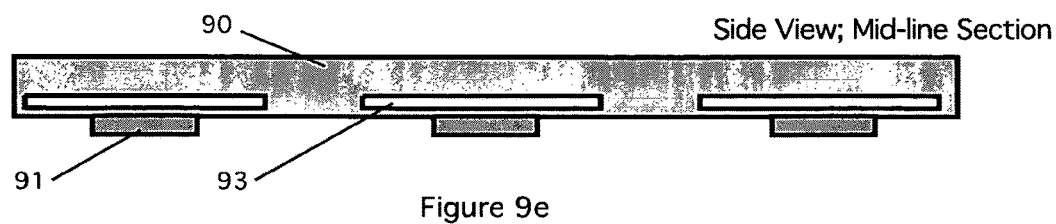

Another structure (FIGS. 9d and 9e) that promotes vibration propagation employs planar or non-planar components of material 93 that exhibit favorable mechanical properties, e.g. higher stiffness or lower damping ratiorelative to the surrounding matrix material. These components, formed for example from metal, high durometer polymer, or certain viscoelastic foams, may be affixed to embedded actuators (FIG. 9d) or located in proximity to surface-mounted actuators (FIG. 9e). These vibration propagation structures may be interrupted, as shown in FIGS. 9d and 9e, or may form a continuous layer throughout the shoe insert.

Common to all the embodiments of the present invention, particularly to the embodiments directed to the bias signal inputting means to apply a stimulation to the mechanoreceptors in the foot, it is important to minimize the discomfort created by the rigidity of the bias signal inputting means. Although many electrodes and actuators are small enough for inclusion in a shoe-based stimulation device, the presence of rigid or semi-rigid objects in a flexing shoe tends to create foot problems, such as sores, ulcers, wounds, etc., in many individuals, especially diabetics. Therefore, the placement of objects in a shoe-based stimulation device preferably avoids bending planes and pressure points.

Figure 10:
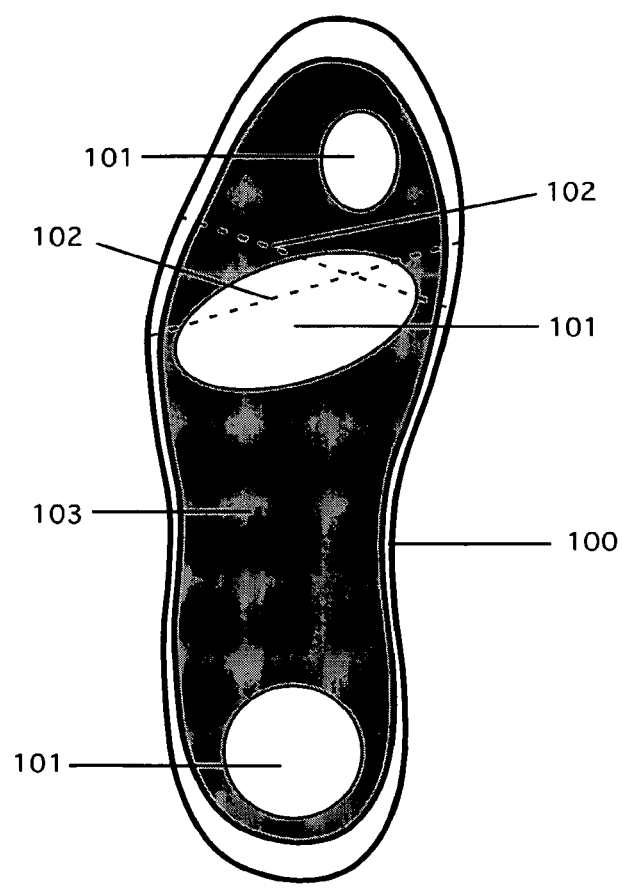
FIG. 10 is an illustration of general bending planes and pressure points from a viewpoint of the underside of a foot.

FIG. 10 depicts a way of incorporating rigid actuators in a shoe insert without creating abnormal pressure points during shoe flexion that normally occurs during walking. A commonly shaped insert 100 for the plantar surface of the foot has areas of high pressure 101 as well as planes of bending 102. In a shoe insole insert, for example, there are typically three high pressure regions and two planes of bending. In other areas, the pressure is generally much less. In addition, little or no bending actually occurs in other regions during use of the insole insert in common activities. By choosing a material, or combination of materials, for the insert body 100 that propagates vibration well, and by placing electrodes or actuators, such as motors, in selected regions 103 outside of the critical areas and away from the insert edge, it is possible to achieve the desired application of stimulation without causing discomfort or adding undue mechanical stress to the electrodes or actuators themselves. In case of motors, minimizing pressure loading thereon lessens the chance of corruption of the desired stimulation signal as well as reduction in motor life The above-mentioned constraints placed on stimulation electrodes and actuators with rigid structure does not apply to electrodes and actuators that are, by nature, flexible and conformable. These include actuators of the electroactive polymer type and others, and electrodes of thin and flexible conductor. Flexible conformable actuators and electrodes may be placed in high pressure regions and bending planes as appropriate.

In the present invention, where electrical bias signals are used to stimulate mechanoreceptors, a variety of electrodes may be used, such as a stick-slip electrode, a disposable electrode, and a reusable electrode, to apply electrical signals to a skin surface. Self-adhesive electrode is an exemplary type of disposable electrode that is commonly available. A common problem associated with traditional self-adhesive electrodes, however, is that they cannot be conveniently incorporated into garments. In general, it would be advantageous for the garment to be able to slide relative to the skin, a motion that is not possible with simple adhesive electrodes incorporated into the garment. To overcome this disadvantage, a novel electrode structure of an embodiment of the present invention, as shown FIG. 11, is described.

Figure 11:
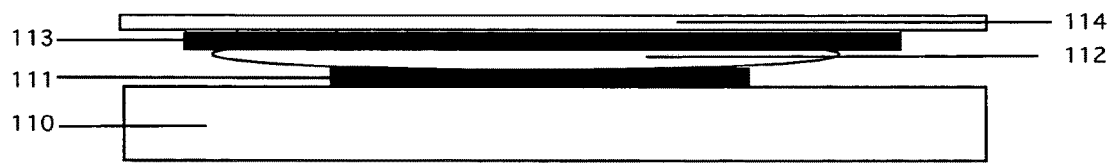
FIG. 11 is a depiction of a moveable sliding electrode system according to one embodiment of the present invention.

As shown in FIG. 11, the skin surface 110 is prepared using traditional methods (e.g. abrading, rubbing, or no preparation at all). Attached to the skin 110 is a conducting electrode 111 with an adhesive backing. A garment layer 114, such as a sock previously mentioned in one of the embodiments of the invention, is fabricated such that it contains an electrode structure 113, woven into or on the garment, on the skin side of the garment. This electrode structure may be temporary or permanent to the garment. Between the two electrodes is placed a thin lubricious and hydrophilic coating 112. This coating serves to conduct electricity as well as allow one electrode to slip pass another without tugging or pulling on the skin. The garment 114 is typically kept snug to the body so that the electrode components are in contact with each other. The lubricious coating may be provided as a separate component that can be easily replaced. The electrode on the garment 114 is typically greater in size than its skin counterpart to allow for relative motion between the components without losing electrical contact. Alternatively, the skin electrode could be the larger of the two.

Figure 12:
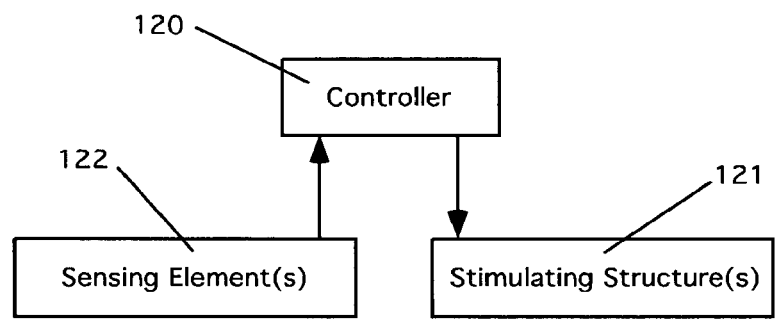
FIG. 12 is a depiction of a method for controlling and adjusting the stimulation parameters as a function of device use according to one embodiment of the current invention.

In the present invention, a controller is responsible for, among other functions, the control of stimulation parameters used to drive the stimulating structures, e.g. electrodes, vibrational actuators, and combinations thereof. A high level diagram of a controller is shown in FIG. 12. Coupled to the controller 120 are one or more stimulating structures 121 and one or more sensing elements or sensors 122. The sensing elements 122 can be used by the controller to modulate the performance of the stimulating structures based on the use of the device.

One example of a sensing element is a pressure sensor which is used by the controller to turn off the device, to place the device in lower power mode when not in use, or to detect a swing phase of a limb. Other examples of sensing elements are accelerometers and force transducers. An exemplary use of a sensing element is to detect if an individual is sitting down, whereby the pressure on a shoe device will be less than when the individual is standing. By sensing the activity of the individual, the controller can, e.g., place the stimulating elements in lower power mode to conserve battery life. Examples of sensors for this application include resistive, capacitive, inductive, piezoelectric, electroactive polymer, silicon-based mechanical sensors, etc.

In addition to powering down the device, sensors could adjust the mode of the device. For example, during walking there is a swing phase where one limb is not in contact with the ground. When not in the swing phase, a limb is in a stance phase where the limb is in contact with the ground. During the swing phase, the controller may switch from providing a subthreshold stimulus for sensory enhancement to a suprathreshold signal for momentary massage action. It is a preferred embodiment that when the device is providing both subthreshold level stimulus and suprathreshold level stimulus, the controller alternately switches between the two levels based on predetermined cycles of swing phase and stance phase, or based on predetermined time cycles. Additionally, the duration and cycle of suprathreshold level stimulation may be affected by the level of battery power source. That is, under power saving mode, the controller may limit the suprathreshold level stimulation, which inherently requires more power to operate than subthreshold level stimulation.

In the same manner, the controller may control the activation of electrical stimulation and vibrational stimulation by controlling their active cycles. In a wearable system of the present invention where a combination of electrical stimulation and vibrational stimulation may be provided, the controller is capable of activating only selected electrodes or vibrational actuators in the manners set forth above so as to conserve energy or to tailor the wearable device for each individual's therapeutic need.

Also, the sensors 122 in FIG. 12 may be used to monitor device performance and to provide a warning signal if actuator elements are not functioning properly, or to make adjustments in the driving signal to account for changes in stimulating element performance over time.

As set forth above, vibrational actuators utilized in the wearable system for neurological stimulation may be of many types, including a rotary motor. Rotary motors are commonly used to produce vibration and are used in such devices as cell phones, pagers, and toys. Their small size makes them amenable to incorporation into sensory enhancement devices. However, unlike these devices, where a single frequency of vibration is acceptable, it is preferred that the present invention produce a wide bandwidth of frequencies. Rotary motors have a rotational velocity, and thus frequency, that is directly linked to the DC voltage applied to them. Hence, it is essential to adapt off-the-shelf rotary motors by using a novel method of the present invention to provide a wider range of vibrational frequencies. One technique for generating a vibration stimulation having a wide range of frequencies, i.e., having broadband noise characteristic, is to drive the motors with a predetermined signal such as shown in FIG. 13.

Figure 13:
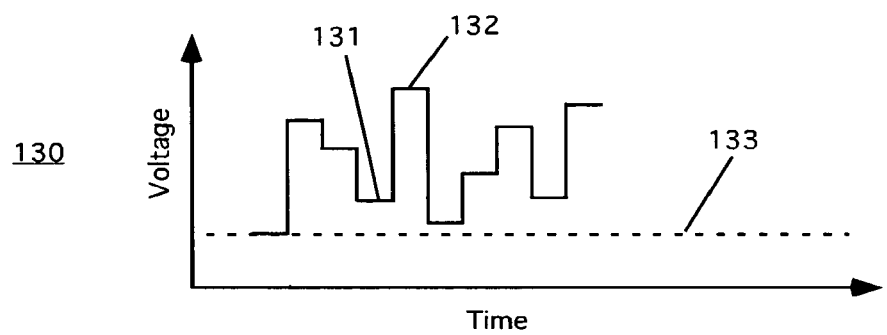
FIG. 13 is a depiction of a sample driving signal used to produce mechanical noise with a platform having a plurality of rotary actuators which have a distinct relationship between their individual driving voltage and output frequency.

FIG. 13 depicts a waveform for single rotary motor actuator within a structure. This waveform 130 is shown on a voltage versus time plot. By changing the voltage in a stepwise fashion, for example from 131 to 132, the motor is driven accelerate or decelerate to a different rotational speed. This changes the frequency of the output vibration for a single motor. The motor is typically slow to respond so it cannot track a rapidly varying signal. Therefore, providing a staircase-like driving signal with each level, like 131 or 132, lasting several milliseconds at least is suitable for achieving the desired vibrational output from the motor. The width of each step of the stepped signal is adjustable and programmable by the controller and its associated signal generator to suit the specification of each rotary motor used as an actuator. The duration of each step of the driving signals is of a time duration sufficiently long to allow each actuator to respond to a driving signal as well as sufficiently short to avoid the actuator fully achieving the rotational speed corresponding to the voltage level of that step. For the type of motors used satisfactorily thus far, the time duration of each step of the driving signal is about, e.g., 2 ms to 8 ms.

In addition, reversing the direction of motor spin, or motor linear movement in the case of a linear motor is used, by changing the polarity of the driving voltage, typically results in a poor response time. To get adequate response out of such a motor, a voltage offset 133 is added to the driving signal. This offset overcomes the inertia of the motor and puts it in a state of readiness. This offset voltage is dependent on the specifications of the motor and, hence, adjustable and programmable by the controller and its associated signal generator to meet different characteristics of motors.

In addition to controlling each actuator in this fashion, there are several other techniques that are used to generate broadband noise out of a plurality of actuators in the wearable system of the present invention. First, the device can encase multiple vibrating elements in a media (e.g. gel) that conducts vibration well. The spatial separation between motors allows for vibration patterns from each motor to constructively and destructively interfere with one another producing additional variation and, thus, noise. The time it takes to propagate the vibration adds to this effect. In addition, some motors in a plurality of motors may be made to rotate in different directions so as to introduce additional randomness in the signal produced by the plurality of actuators in the present invention.

Figure 14A:
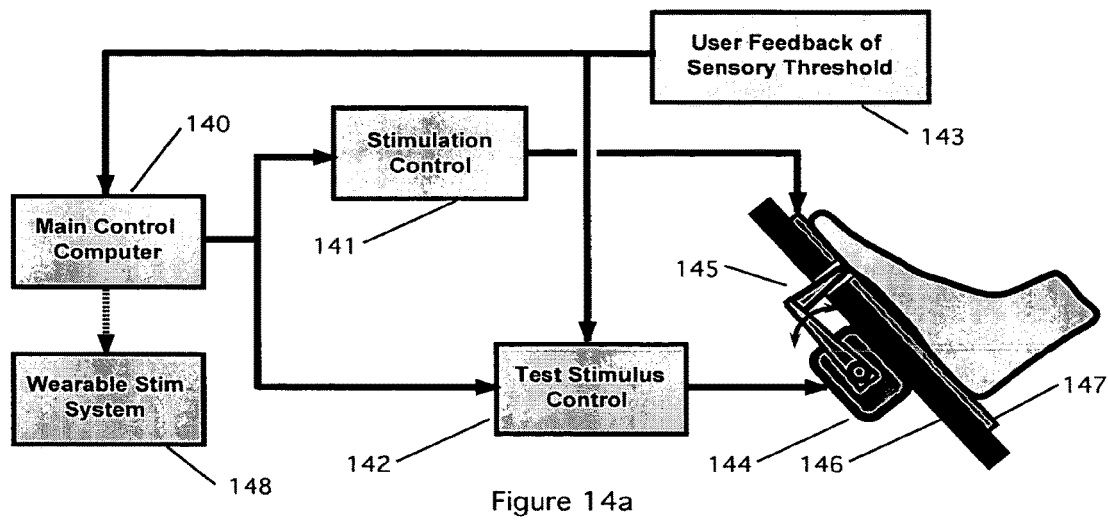
FIG. 14a depicts a system for tuning and optimizing a wearable neurological stimulation device of the present invention.
Figure 14B:
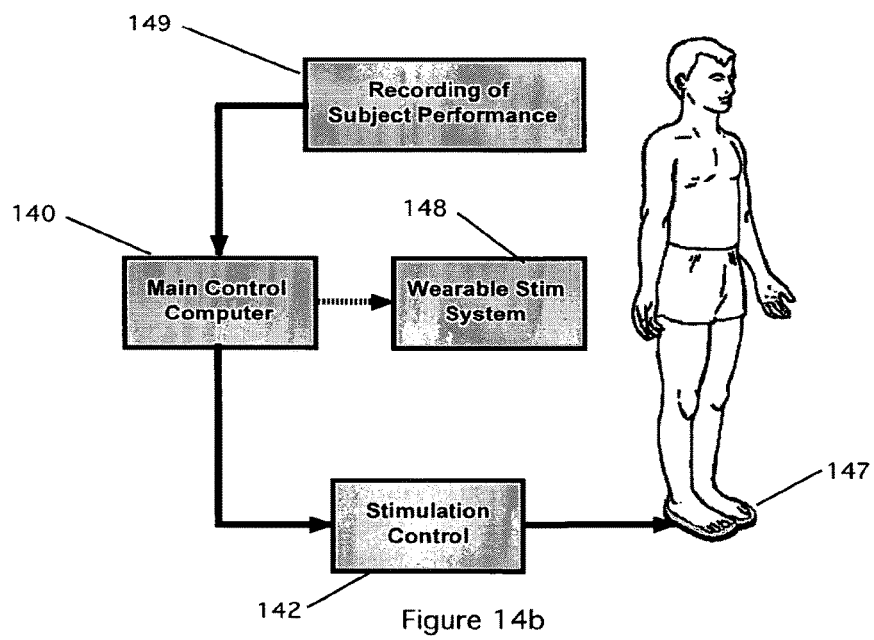
FIG. 14b depicts a system for tuning and optimizing a wearable neurological stimulation device of the present invention while a wearer of the device is performing a predetermined task.

FIGS. 14*a-b* depict additional embodiments of the present invention. To achieve the highest degree possible of therapeutic benefit from the neurological stimulation described herein, it may be beneficial to customize or otherwise tune stimulation parameters to the particular needs of the individual user.

One such system, FIG. 14*a*, involves the individual in a series of sensory performance tests while stimulation settings are varied. The individual places an area to be tested, for example the plantar surface of the foot, on a support platform 146 which has a neurological stimulation delivery device 147 attached to it. A main control computer 140, with custom software and laboratory interfaces, controls all aspects of the test and subsequent analysis. As an example of one such test, the computer 140 sets particular stimulation parameters in a programmable stimulation controller 141. The computer 140 also selects a series of test stimuli to be presented via a programmable test stimulus control 142. The stimulus controller 142 in turn causes a stimulus actuator 144 and stimulus presentation device 145 to present the test stimulus to the individual. Neurological stimulation is provided to the individual in the vicinity of the test stimulus via the stimulation device 147. The individual's responses to the test stimulus, for example whether it was sensed or not, are recorded by appropriate instrumentation 143 and made available to the main control computer 140, and perhaps also directly to the test stimulus control 142.

A process of adjusting neurological stimulation parameters while monitoring changes in sensory function will allow optimal stimulation parameters to be selected for this individual. These parameters will preferably be downloaded or otherwise communicated to the control means of the wearable stimulation system 148.

The system described in FIG. 14*a* can also be used to determine the sensory threshold of an individual in the anatomical area of interest. In this use, the neurological stimulation device is turned off. A series of test stimuli at different levels are presented by the stimulus actuator 144 and presentation device 145. The levels are adjusted until the individual identifies a stimulus level as just barely sensed. Alternatively, the stimulation device 147 itself can be used to deliver test stimuli rather than neurological stimulation.

A second such system, FIG. 14*b*, also is used to tune stimulation parameters to the needs of the individual. In this system, a main control computer 140 again controls the test, using a programmable stimulation controller 142. In this system, however, the individual is instructed to perform a task while the system presents a variety of stimulation patterns. The individual's performance in this task is recorded by appropriate instrumentation 149. These performance measures are made available to the control computer 140. Stimulation parameters are adjusted to achieve the best task performance by the individual. As before, the optimal stimulation parameters for the individual will preferably be downloaded or otherwise communicated to the control means of the wearable stimulation system 148.

Figure 16A:
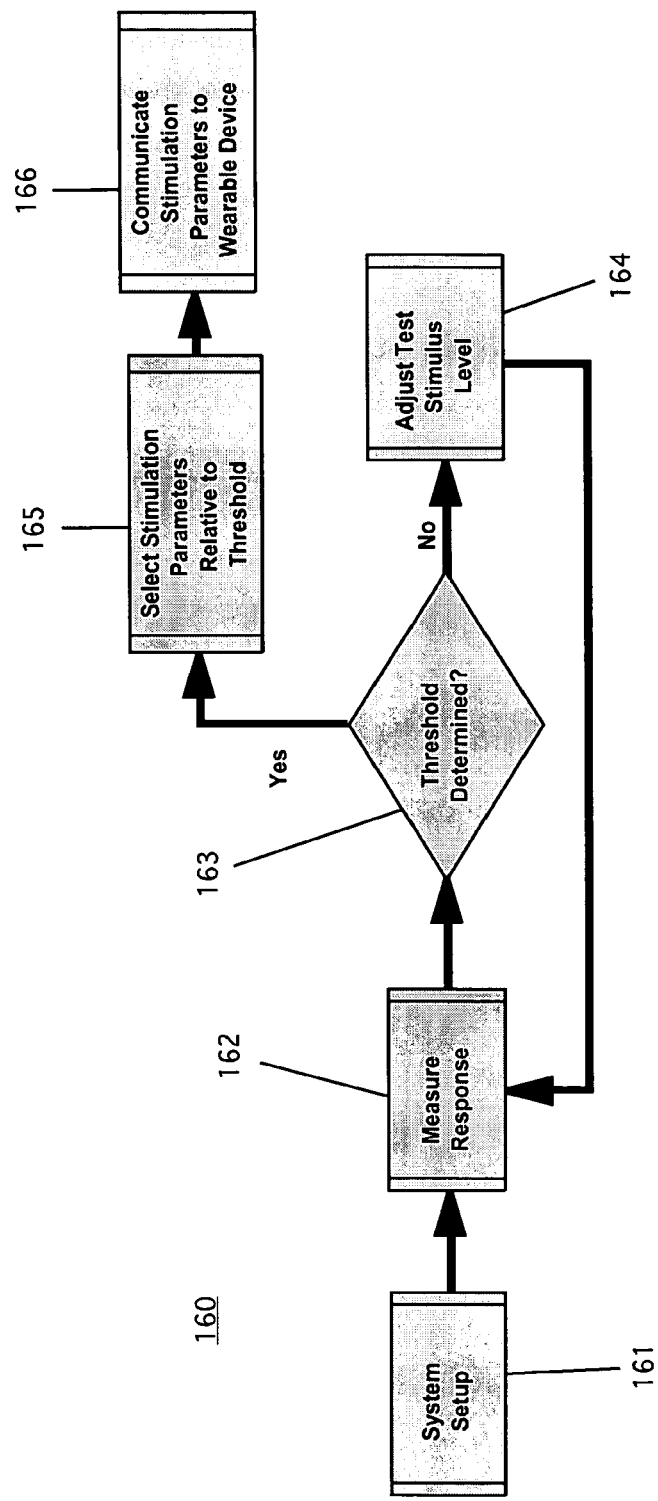
FIG. 16a is a block diagram of a method for determining sensory threshold of an individual.

A preferred method for employing the apparatuses shown in FIG. 14 for determining sensory threshold can be better understood by referring to FIG. 16*a*. Following a step 161 of setting up equipment, instructing the individual, and selecting an initial level for the test stimulus, a measurement 162 of the individual's ability to sense the stimulus is made. A determination 163 is made as to whether that stimulus level is the sensory threshold. If additional testing is required, the test stimulus level is adjusted 164 and the test is repeated 162. When the threshold level has been successfully determined, the appropriate stimulation parameters are selected relative to the threshold 165. These parameters are then communicated to the wearable stimulation device 166.

Figure 16B:
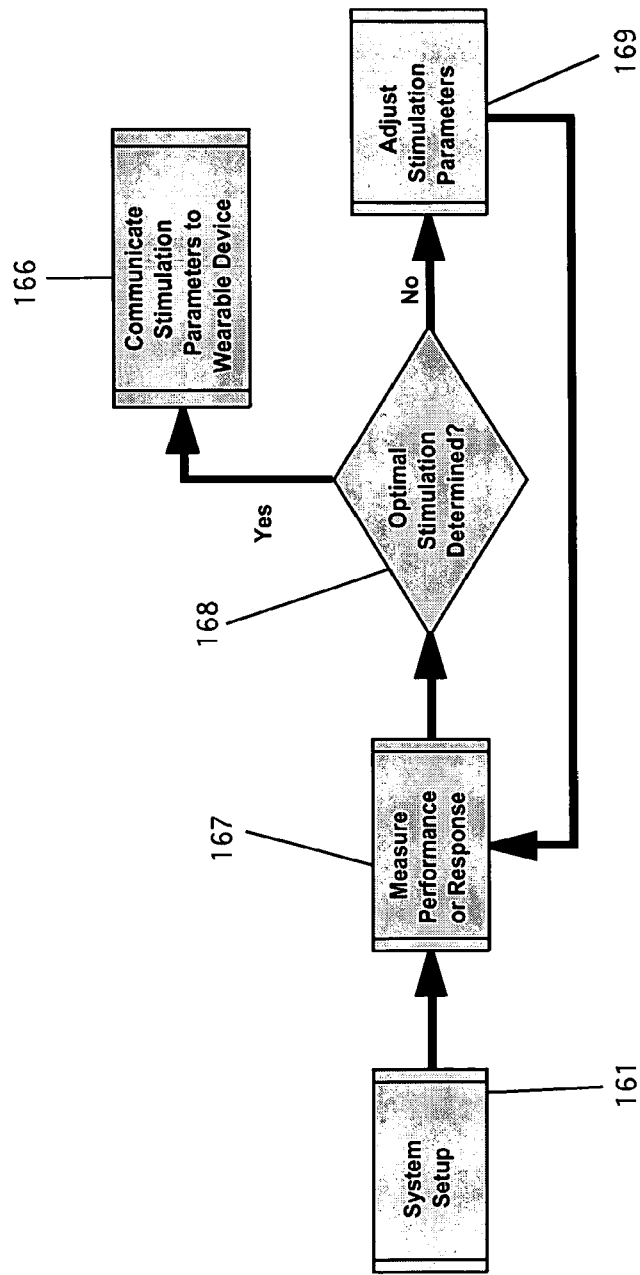
FIG. 16b is a block diagram of a method for determining an optimal stimulation for an individual.

A preferred method for employing the apparatuses shown in FIG. 14 for optimizing stimulation can be better understood by referring to the method of FIG. 16*b*. Following a step 161 of setting up equipment, instructing the individual, and selecting an initial trial level of stimulation, a measurement 167 of the individual's performance in a specified sensorimotor task is made. A determination 168 of whether that performance is the best possible is made. If it is determined that the performance is not yet optimal, the stimulation parameters are adjusted 169 based on results from trials already completed. Additional performance measurements 167 are then made. This process is repeated until a condition of optimality is achieved. At that time, the optimization system will be caused to communicate 166 the optimal stimulation parameters to the wearable device.

In the method of FIG. 16*b*, the types of sensorimotor tasks used to optimize the therapeutic stimulation include tactile sensitivity tests, joint angle perception tests, balance tests, walking and other gait tests, and other motor skills.

In the method of FIG. 16*b*, the types of measures made while the sensorimotor task is being performed include: direct verbal responses from the individual; measurements made from biomechanical instrumentation such as force plates, motion tracking systems, and goniometers; neurophysiology measurements made by monitoring electrical activity on sensory or motor neurons emanating from the test area; and neurophysiology measurements made by monitoring brain activity with instruments such as EEG, fMRI, etc.

Figure 15:
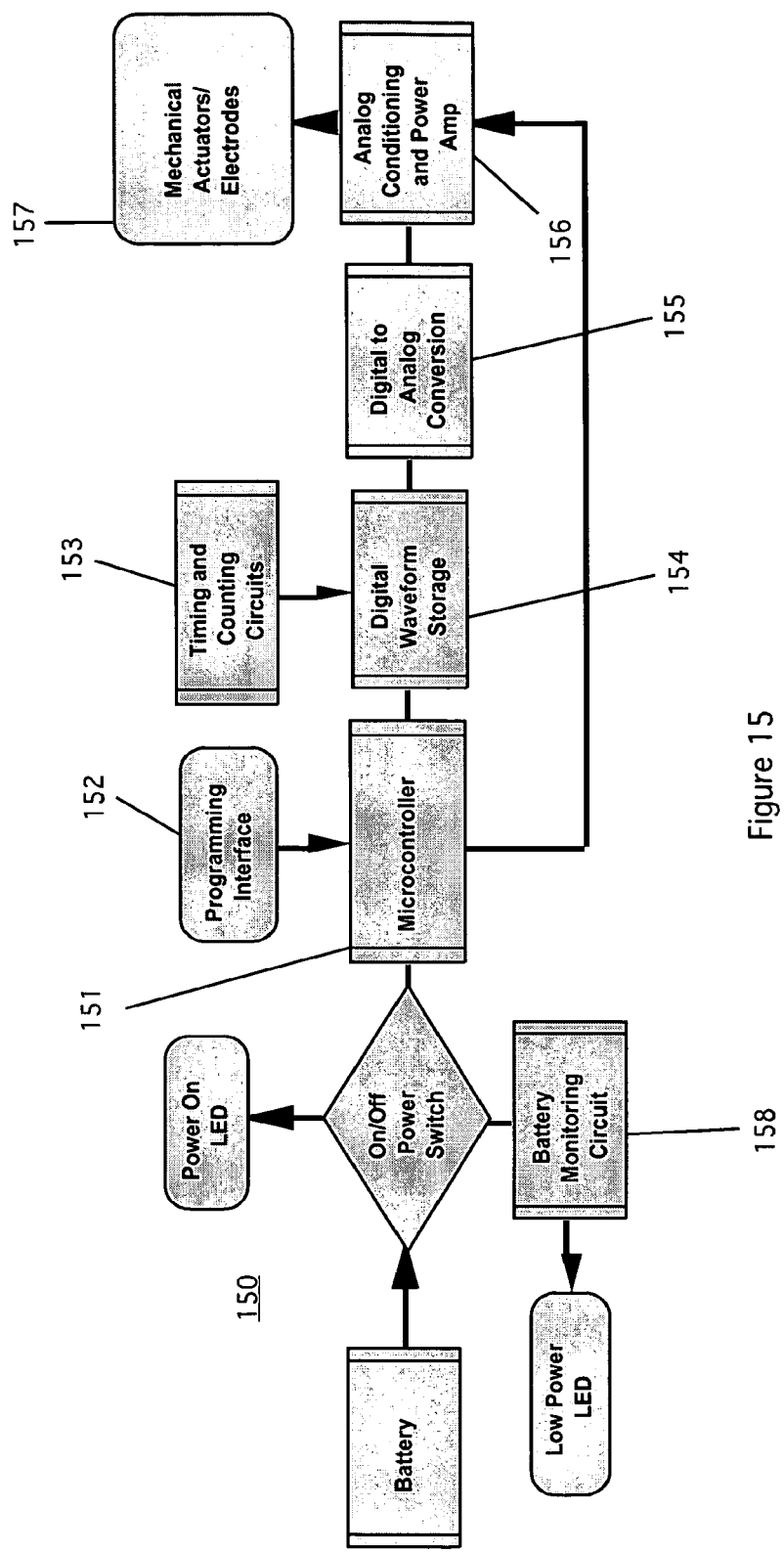
FIG. 15 is a high-level block diagram of the electrical components of an embodiment of the present invention.

The controller utilized in the present invention generally includes, for example, a CPU, memory, such as flash memory, RAM, EPROM, PROM, EDO, FP, a serial or parallel communication port, DC/DC converter, A/D converter (ADC), D/A converter (DAC), programmable logic device, and amplifiers. An example of the controller and its associated components can be seen in FIG. 15, which includes a microcontroller 151, a programming interface 152, such as serial or parallel communication interface, a digital waveform storage 154 (i.e. memory), which may also be used as a shared system memory, DAC 155 for converting digital bias signal to analog bias signal, analog conditioning and power amplifier for conditioning and amplifying the bias analog signal to a level suitable for driving mechanical actuators or electrodes 157, a timing and counting circuit for 153 for various system timing needs, and a battery monitoring circuit 158. The diagram also includes battery, on/off switch, and status light indicators. The signal generator may be viewed as an integral part of the controller or a separately grouped component, including, for example, ADC, DAC, memory, such as of the previously mentioned types, amplifiers. The details of these electronic and electrical components are not described herein as they should be apparent to persons in the art to select the proper electrical and electronic hardware to implement combination to implement the controller, signal generator, communication interface, batter power source, and other features of the present invention disclosed herein.

All embodiments of the present invention disclosed herein utilize a signal generator to provide a driving signal to drive an electrical stimulator, a vibrational actuator, or a combination thereof. The bias signal for driving an electrical stimulator of the present invention is composed of one or more frequencies with a bandwidth of greater than 0 Hz to about 10 KHz, preferably greater than 0 Hz to about 5 KHz, and more preferably greater than 0 Hz to about 1 KHz. Further, each electrical stimulator of the present invention provides an electrical stimulation to the skin with a current density in a range of between greater than 0 to 10 about $mA/in^2$, preferably between greater than 0 to about 1 $mA/in^2$, and more preferably between greater than 0 to about 0.5 $mA/in^2$.

The bias signal for driving each vibrational actuator is composed of one or more frequencies with a bandwidth of greater than 0 Hz to about 1 KHz, preferably of greater than 0 Hz to about 500 Hz, and more preferably of greater than 0 Hz to about 100 Hz. Further, the bias signal for driving the vibrational actuator selected to produce a mechanical stimulation of greater than 0 $lbs/in^2$ to about 10 $lbs/in^2$, preferably greater than 0 lbs/in² to about 5 lbs/in², and more preferably greater than 0 lbs/in² to about 1 lb/in².

The amplitude of the driving signal for each type of stimulator, electrical or vibrational, used in all embodiments of the present invention is dependent on the electrical characteristics of each stimulator as well as the neurological condition of the skin area of the foot and ankle of the individual utilizing the wearable system of the present invention. The subthreshold and suprathreshold levels of stimulation are relative from one stimulation site to another on the foot and ankle as well as from one individual to another. Generally, subthreshold level is about 5 to 50% below a measured sensory threshold level, with a preference of between 10 and 30%. On the other hand, suprathreshold level is about 10% to 1000% above a measured threshold level, preferably 20%-500%, more preferably 20% to 100% above a measure threshold.

In the above-described embodiments one through seven above, the controller, signal generator, communication interface port, recharging port, and battery power source are generally grouped together in one housing or integrated with a platform containing stimulators. However, it should be noted that these general components can be grouped separately and housed in a separate housing. For example, the controller, the signal generator and the communication interface port hardware can be provided on one main printed circuit board, while the battery and its charging port are packaged in a separate housing and located at a remote location from the main board. In another example, a single controller, signal generator, and battery power source could be used to control and power stimulation devices on each lower extremity. This single controller would be located centrally, e.g. on the belt of a garment, with cables communicating with the stimulation devices located on the left and right sides.

In the contemplated embodiments of the present invention, it is generally preferred that the stimulators, i.e. electrical or vibrational actuators, are coupled to the signal generator and controller by an electrical conductor, such as a metallic wire or a composite conductor. However, in an alternative embodiment, the coupling is wireless, such as inductive coupling and RF coupling. In the case of wireless coupling between the stimulators and the controller and signal generator, the stimulator has its own battery power source, a receiver for wirelessly receiving a stimulus signal from the signal generator, and an amplifier to amplify the received signal to a sufficiently high level to drive a stimulator to provide a stimulation to a neuroreceptor area on an individual. An advantage to this wireless coupling is the placement of the controller, battery, etc on any part of the body or accessory worn on the body, such as fanny pack, belt, pocket, etc. Further, by having a dedicated battery to power the stimulators, the wearable system may last longer on one battery charge.

The various stimulators supporting platforms, such as a shoe insert, disposable pad, shoe, foot and ankle harness, and sock and insole combination, optionally include means for providing heat therapy to the foot, ankle, or both. The typical purpose of heat therapy is to increase local blood flow and to improve the thermal status of the tissue. Combining heat therapy with neurological stimulation in the present invention adds to the overall value of the system, especially for those individuals such as diabetics who commonly suffer loss of both sensory function and blood flow in the extremities.

Heat therapy may be provided by a thermal radiation source, such as IR, ultrasound, or a heating filament controlled by the controller. An example of a heater 86 with a neurological stimulation device of the present invention is shown in FIG. 8a. The placement of the heater 86 is preferably away from the electrical and vibrational stimulators on a platform to avoid heat stress to the stimulators and as close to the skin as possible, such as shown in FIG. 8b where heater 86 is located close to the top surface of the insole for maximum heat transfer. Electrical power for driving the heater may be provided by the same power source for the controller, etc. or by an optional extra battery pack. The battery power source may include a power converter, not shown, to support the current or voltage requirement of the heater. Further, the controller may include an additional signal generator to provide an ultrasonic driving signal in the MHz range, if an ultrasonic heating means is included.

In every embodiment of the present invention, one or more battery power sources, preferably rechargeable, are used so as to add to the mobility and portability of the wearable system providing neurological stimulation. Types of batteries usable in the present invention include an alkaline, NiCad, a rechargeable lithium-ion, polymer, gel, and nickel metal hydride. Similarly, other portable power sources such as fuel cells may be used to power the present invention.

Additional power recovery technologies are available that could advantageously be added to the present invention. Certain materials and components have been shown to be able to generate usable electrical power from excess energy expended during striding. Similarly, photoelectric cells can generate electrical power when irradiated with light. Either or both power recovery technologies could be used in the present invention to provide a partial or full recharge to the internal batteries of the stimulation system.

The actuators discussed thus far have been active actuators that require an electrical power source and driving signal to provide a stimulating vibration to a mechanoreceptor site. However, the invention is not limited to the use of active devices. Passive vibrational actuators may also be used. Passive mechanical actuators are constructed from materials that generate mechanical vibrations as they are compressed by body weight during locomotion, etc. Such mechanisms incorporate a bias structure that returns the actuator to its original position when the load is removed. As compression or decompression takes place, the actuator emits a vibration. That is, during striding, the passive actuator structure is repeatedly compressed by the application of body weight, and returned to its original position. Consequently, useful mechanical vibrations are generated.

The foregoing specific embodiments of the present invention as set forth in the specification herein are for illustrative purposes only. Various deviations and modifications can be made within the spirit and scope of this invention, without departing from the main theme thereof. It will be appreciated by persons skilled in the art that the present invention is not limited by what has been particularly shown and described herein above.

What is claimed is:

1. A wearable system for neurological stimulation of a human foot, the system comprising:
   a platform having at least one vibrational actuator adapted to apply a mechanical stimulation to mechanoreceptors in the foot;
   at least one signal generator adapted to provide at least one driving signal to drive the at least one vibrational actuator;

a controller configured to control the at least one signal generator and the at least one vibrational actuator;

a sensor coupled to the controller, the sensor configured to sense activity of the foot; and a power source providing electrical energy to the controller and the at least one signal generator, wherein the platform is a removable insole insert of a shoe, and wherein the controller is configured to adjust the at least one driving signal provided by the at least one signal generator to transition the at least one vibrational actuator between providing, to the mechanoreceptors in the foot, a mechanical stimulation having a subthreshold magnitude based on a first activity of the foot sensed by the sensor and a mechanical stimulation having a suprathreshold magnitude based on a second activity of the foot sensed by the sensor, the first activity being different from the second activity.

2. The wearable system of claim 1, wherein the removable insole insert comprises a flexible matrix material filled with rigid beads, and wherein the at least one vibrational actuator comprises a plurality of vibrational actuators disposed underneath the removable insole insert such that the removable insole insert is optimized for transmitting mechanical vibration to a plantar surface of the foot.

3. The wearable system of claim 1, wherein the removable insole insert comprises a flexible matrix material filled with rigid beads, and wherein the at least one vibrational actuator comprises a plurality of vibrational actuators embedded within the flexible matrix material such that the removable insole insert is optimized for transmitting mechanical vibration to a plantar surface of the foot.

4. The wearable system of claim 1, wherein the removable insole insert comprises a flexible matrix material enclosing a vibration transmitting structure and the at least one vibrational actuator, and wherein the flexible matrix material is optimized for transmitting mechanical vibration to surfaces of the foot.

5. The wearable system of claim 1, wherein the at least one vibrational actuator comprises a plurality of vibrational actuators disposed on the removable insole insert at a predetermined spatial separation between each of the plurality of vibrational actuators to induce random mechanical vibration by manipulating a phase of the at least one driving signal of each of the plurality of vibrational actuators.

6. The wearable system of claim 1, wherein the at least one vibrational actuator comprises a plurality of vibrational actuators adapted to create a mechanical vibration when being electrically biased, and wherein the controller is configured to operate at least a first one of the plurality of vibrational actuators in a first direction of spin and at least a second one of the plurality of vibrational actuators in a second direction of spin so as to induce random vibrational mechanical stimulation.

7. A wearable system for neurological stimulation of a human foot, the system comprising:

a platform having at least one vibrational actuator adapted to apply a mechanical stimulation to mechanoreceptors in the foot;

at least one signal generator adapted to provide at least one driving signal to drive the at least one vibrational actuator;

a sensor configured to sense a pressure on the foot and to sense activity of the foot, the activity of the foot including at least one of: (i) movement of the foot between a swing phase and a stance phase; (ii) position change of the foot between a seated position and a standing position; (iii) acceleration of the foot; or (iv) any combination of (i), (ii), and (iii);

a controller configured to control the at least one signal generator and the at least one vibrational actuator; and a power source providing electrical energy to the controller and the at least one signal generator, wherein the platform is a removable insole insert of a shoe, and wherein the at least one driving signal to drive the at least one vibrational actuator is composed of one or more frequencies with a bandwidth of greater than 0 Hz to about 1 KHz and wherein the controller is configured to adjust the at least one driving signal provided by the at least one signal generator based on the sensed pressure on the foot to thereby cause the at least one vibrational actuator to provide: (i) at a first time, a first mechanical stimulation having a subthreshold magnitude when the pressure on the foot is greater than at least a pressure threshold; (ii) at a second time after the first time, a second mechanical stimulation having a suprathreshold magnitude when the pressure on the foot is less than at least the pressure threshold; and (iii) at a third time after the second time, a third mechanical stimulation having a subthreshold magnitude when the pressure on the foot is greater than at least the pressure threshold.

8. The wearable system of claim 7, wherein the at least one driving signal to drive the at least one vibrational actuator is composed of one or more frequencies with a bandwidth of greater than 0 Hz to about 500 Hz.

9. The wearable system of claim 8, wherein the at least one driving signal to drive the at least one vibrational actuator is composed of one or more frequencies with a bandwidth of greater than 0 Hz to about 100 Hz.

10. A wearable system for neurological stimulation of a human foot, the system comprising:

a removable insole insert comprising:

a platform having at least one vibrational actuator adapted to apply a mechanical stimulation to mechanoreceptors in the foot;

at least one signal generator adapted to provide at least one driving signal to drive the at least one vibrational actuator;

a controller configured to control the at least one signal generator and the at least one vibrational actuator;

a sensor coupled to the controller to sense activity of the foot; and a power source providing electrical energy to the controller and the at least one signal generator, wherein the controller is programmable and wherein the controller is configured to adjust the at least one driving signal provided by the at least one signal generator to transition the at least one vibrational actuator between providing, to the mechanoreceptors in the foot, a mechanical stimulation having a subthreshold magnitude and a mechanical stimulation having a suprathreshold magnitude based on the activity of the foot sensed by the sensor.

11. The wearable system of claim 10, further comprising a thermal radiation source configured to provide heat therapy to the foot.

12. The wearable system of claim 10, wherein the at least one signal generator provides a non-deterministic random signal driving the at least one vibrational actuator.

13. The wearable system of claim 10, wherein the at least one signal generator provides a signal of a predetermined at least one repetitive pattern and series of patterns.

14. The wearable system of claim 10, wherein the at least one driving signal has a controllable signal amplitude, a controllable frequency content, a controllable waveform shape, and a controllable repetition.

15. The wearable system of claim 10, wherein the at least one vibrational actuator comprises a plurality of vibrational actuators, and wherein the controller is adapted to control individually each of the plurality of vibrational actuators so as to effect individually controllable amplitude, individually controllable frequency content, individually controllable waveform shape, and individually controllable repetition of the mechanical stimulation provided by each of the plurality of vibrational actuators.

16. The wearable system of claim 10, wherein the controller controls the at least one signal generator and the at least one vibrational actuator to provide the mechanical stimulation having the subthreshold magnitude so as to effect sensory enhancement.

17. The wearable system of claim 10, wherein the controller controls the at least one signal generator and the at least one vibrational actuator to provide the mechanical stimulation having the suprathreshold magnitude so as to effect therapeutic massage and improvement of blood flow.

18. The wearable system of claim 10, wherein the controller controls the at least one signal generator and the at least one vibrational actuator to alternatively provide the mechanical stimulation having the subthreshold magnitude and the mechanical stimulation having the suprathreshold magnitude so as to effect sensory enhancement, therapeutic massage and improvement of blood flow.

19. The wearable system of claim 10, wherein the at least one vibrational actuator comprises a first vibrational actuator and a second vibrational actuator, and wherein the controller controls the at least one signal generator, the first vibrational actuator, and the second vibrational actuator, the first vibrational actuator providing the mechanical stimulation having the subthreshold magnitude and the second vibrational actuator providing the mechanical stimulation having the suprathreshold magnitude, so as to effect sensory enhancement, therapeutic massage and improvement of blood flow.

20. The wearable system of claim 1, wherein the controller is configured to differentiate among different activities of the foot based on an output of the sensor, the activities including (a) a movement or acceleration of the foot and (b) a position change of the foot.

21. The wearable system of claim 20, wherein the movement includes movement of the foot during a gait between a swing phase and a stance phase and the position change includes a change in a position of the foot between a seated position and a standing position.

* * * * *

UNITED STATES PATENT AND TRADEMARK OFFICE
CERTIFICATE OF CORRECTION

PATENT NO.        : 10,076,460 B2                                    Page 1 of 1
APPLICATION NO.   : 13/674769
DATED             : September 18, 2018
INVENTOR(S)       : Harry et al.

It is certified that error appears in the above-identified patent and that said Letters Patent is hereby corrected as shown below:

In the Specification

Column 1, Line 12, insert:
--STATEMENT REGARDING FEDERALLY SPONSORED RESEARCH OR DEVELOPMENT--

Column 1, Lines 13-16, should be replaced with the following:
--This invention was made with government support under Contract Numbers AG008812, AG004390, DK060295, HD040035 and HD037880 awarded by the National Institutes of Health. The government has certain rights in the invention.--

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*